(12) United States Patent
Bryan

(10) Patent No.: US 10,071,911 B2
(45) Date of Patent: Sep. 11, 2018

(54) SELF ASSEMBLING BETA-BARREL PROTEINS POSITION NANOTUBES

(71) Applicant: Prolume, Ltd., Lakeside, AZ (US)

(72) Inventor: Bruce Bryan, Beverly Hills, CA (US)

(73) Assignee: PROLUME, LTD., Pinetop, AZ (US)

( * ) Notice: Subject to any disclaimer, the term of this patent is extended or adjusted under 35 U.S.C. 154(b) by 0 days.

(21) Appl. No.: 14/772,665

(22) PCT Filed: Mar. 5, 2014

(86) PCT No.: PCT/US2014/020869
§ 371 (c)(1),
(2) Date: Sep. 3, 2015

(87) PCT Pub. No.: WO2014/138286
PCT Pub. Date: Sep. 12, 2014

(65) Prior Publication Data
US 2016/0016801 A1    Jan. 21, 2016

Related U.S. Application Data

(60) Provisional application No. 61/773,109, filed on Mar. 5, 2013.

(51) Int. Cl.
| | |
|---|---|
| B82Y 30/00 | (2011.01) |
| C01B 31/02 | (2006.01) |
| C08H 1/00 | (2006.01) |
| C07K 14/005 | (2006.01) |
| C08J 9/12 | (2006.01) |
| C12N 9/02 | (2006.01) |
| C01B 32/158 | (2017.01) |
| C01B 32/16 | (2017.01) |
| B82Y 40/00 | (2011.01) |

(52) U.S. Cl.
CPC .......... *C01B 31/0226* (2013.01); *B82Y 30/00* (2013.01); *C01B 32/158* (2017.08); *C01B 32/16* (2017.08); *C07K 14/005* (2013.01); *C08H 1/00* (2013.01); *C08J 9/122* (2013.01); *C12N 9/0069* (2013.01); *B82Y 40/00* (2013.01); *C08J 2383/00* (2013.01); *C12N 2770/00051* (2013.01)

(58) Field of Classification Search
CPC .................................................. B82Y 30/00
See application file for complete search history.

(56) References Cited

U.S. PATENT DOCUMENTS

| 6,495,352 B1 | 12/2002 | Brinker et al. |
| 7,238,729 B2 | 7/2007 | Rolison et al. |
| 2004/0024076 A1 | 2/2004 | Davis |
| 2008/0274155 A1 | 11/2008 | Barton et al. |
| 2009/0181402 A1 | 7/2009 | Finn et al. |
| 2010/0240146 A1 | 9/2010 | Sommer-Knudsen et al. |
| 2012/0003694 A1 | 1/2012 | Movileanu et al. |
| 2012/0083012 A1 | 4/2012 | Chang et al. |
| 2012/0141767 A1 | 6/2012 | Chen-Yang et al. |

OTHER PUBLICATIONS

Tarek et al., 2003, Molecular Dynamics Investigation of an Oriented Cyclic Peptide Nanotube in DMPC Bilayers, Biophysical Journal, 85: 2287-2298.*
Bayley et al., 2001, Stochastic sensors inspired by biology, Nature, 413: 226-230.*
Ostojic, 2012, Optical Properties of Assembled Single-Walled Carbon Nanotube Gels, ChemPhysChem, 13: 2102-2107.*
Ostojic et al., 2012, Biomolecule-Directed Assembly of Self-Supported, Nanoporous, Conductive, and Luminescent Single-Walled Carbon Nanotube Scaffolds, Small, 8(12): 1840-1845.*
Li et al., 2011, Three-dimensional arrayed amino aerogel biochips for molecular recognition of antigens, Biomaterials, 32: 7347-7354.*
Harper-Leatherman et al., 2012, Simplified Procedure for Encapsulating Cytochrome c in Silica Aerogel Nanoarchitectures while Retaining Gas-Phase Bioactivity, Langmuir, 28: 14756-14765.*
Beke et al., 2008, a Theoretical Comparison of Self-Assembling _- and _-Peptide Nanostructures: Toward Design of _-Barrel Frameworks, ACSNano, 2(3): 545-553.*
Fu et al., 2009, Induced _-Barrel Formation of the Alzheimer's A_25-35 Oligomers on Carbon Nanotube Surfaces: Implication for Amyloid Fibril Inhibition, Biophysical Journal, 97: 1795-1803.*
Korhonen et al., 2011, Inorganic Hollow Nanotube Aerogels by Atomic Layer Deposition onto Native Nanocellulose Templates, ACSNano, 5(3): 1967-1974.*
Bayley, H. et al., "Functional Engineered Channels and Pores (Review), Molecular Membrane Biology", 2004, vol. 21, pp. 209-220 [retrieved on Sep. 5, 2014]; Retrieved from the Internet: URL:http:www.ncbi.nlm.nih.gov/pubmed/15371010>DOI: 10. 1080/09867680410001716853>; p. 210, paragraphs 1, 3; p. 211, paragraph 5; p. 214, paragraph 2; p. 215, paragraph 1.

(Continued)

*Primary Examiner* — Amber D Steele
(74) *Attorney, Agent, or Firm* — Swanson & Bratshun, L.L.C.

(57) ABSTRACT

The present invention relates to the extraordinary properties of recently discovered nanotubes. This disclosure teaches a method for using barrel proteins acting as scaffolds to guide assembly of nanotubes, and using nano-molecular molding jigs to format the nanotubes into stable arrays with the precise geometric architecture desired. This disclosure teaches nanotube technology with principles of protein folding and aggregated self-assembly. In certain embodiments, the disclosure teaches using highly modified barrel proteins to form hydrophobic and hydrophilic channels that guide the nanotubes into their centers, or other geometric patterns utilizing silicone aerogel to form nano-molecular molds, jigs, and surfaces to position nanotubes in precise geometric arrangements and arrays. This disclosure teaches new uses of barrel proteins as self-assembling molding tools to develop new nanometer scaled devices and their uses herein.

1 Claim, 22 Drawing Sheets

Specification includes a Sequence Listing.

(56) References Cited

OTHER PUBLICATIONS

International Search Report and Written Opinion for PCT/US14/20869, dated Jul. 30, 2014, 39 pages.
Schulz, G., "β-Barrel membrane proteins", Current Opinion in Structural Biology, 2000, vol. 10, pp. 443-447 [retrieved on Sep. 5, 2014]; Retrieved from the Internet:URL:http://www.physics.uoguelph.ca/~dutcher/download/nano_4100/cd/lipids%20proteins%20and%20membranes/schulz_CurrOpinStrucBiol_00_beta%20barrels.pdf.

* cited by examiner

FIG. 7

Residues 6-15 of SEQ ID NO: 8
Residues 59-68 of SEQ ID NO: 7
Residues 41-50 of SEQ ID NO: 7
Residues 18-27 of SEQ ID NO: 7
Residues 4-13 of SEQ ID NO: 7
Residues 19-28 of SEQ ID NO: 5
Residues 7-16 of SEQ ID NO: 5
Residues 24-33 of SEQ ID NO: 4
Residues 11-20 of SEQ ID NO: 4
Residues 12-21 of SEQ ID NO: 3
Residues 25-34 of SEQ ID NO: 3
Residues 24-33 of SEQ ID NO: 2
Residues 9-18 of SEQ ID NO: 2
Residues 35-44 of SEQ ID NO: 1
Residues 23-32 of SEQ ID NO: 1
Residues 1-10 of SEQ ID NO: 1 connect junctions   connect   connect

Structure-based design of Hcp1 nanotubes

Ballister E R et al. PNAS 2008;105:3733-3738

SELF ASSEMBLING BETA-BARREL PROTEINS POSITION NANOTUBES

CROSS REFERENCE TO RELATED APPLICATIONS

This application is a 35 U.S.C. § 371 National Stage Entry of International Application Serial No. PCT/US2014/020869, filed on Mar. 5, 2014 (WO 2014/138286), which application claims the benefit of U.S. Provisional Application Ser. No. 61/773,109, filed on Mar. 5, 2013, which is incorporated by reference in its entirety.

SEQUENCE STATEMENT

Incorporated by reference herein in its entirety is the Sequence Listing entitled "Sequence_Listing_ST25_0551_02_03US" created Oct. 9, 2017, 2017, size of 4 kilobyte.

TECHNICAL FIELD

The present invention relates to the extraordinary properties of recently discovered nanotubes. Many types of nanotubes have been manufactured using many different kinds of materials, each possessing different properties. Many of these nanotubes have yet to be explored and exploited. Carbon nanotubes may be single walled or multi-walled; non-carbon nanotubes have useful properties as well. This disclosure teaches how to place the nanotubes in the desired geometry in three dimensional space and make individual stable electrical or otherwise precise connections to position the nanotubes for maximal utility. This disclosure teaches a method for using barrel proteins acting as scaffolds to guide assembly of nanotubes, and using nano-molecular molding jigs to format the nanotubes into stable arrays with the precise geometric architecture desired. This disclosure teaches nanotube technology with principles of protein folding and aggregated self-assembly. In certain embodiments, the disclosure teaches using highly modified barrel proteins to form hydrophobic and hydrophilic channels that guide the nanotubes into their centers, or other geometric patterns utilizing silicone aerogel to form nano-molecular molds, jigs, and surfaces to position nanotubes in precise geometric arrangements and arrays. This disclosure teaches new uses of barrel proteins as self-assembling molding tools to develop new nanometer scaled devices and their uses herein.

BACKGROUND

Nanotubes possess many unique properties quite useful in many devices, specifically exemplified in electronic devices. One problem of commercialization is the absence of methods to align the nanotubes easily and have them spontaneously form in the proper arrangement.

Difficulties with assembly result from the properties of the nanotubes themselves; they are small, on the order of 0.6 to several nanometers in diameter. During the manufacture process, nanotubes lengths differ. Additionally, when nanotubes are manufactured, they tend to self-aggregate given their hydrophobic nature. Nanotubes prefer environments that do not contain water, provided the nanotubes are not chemically derivatized with polar groups, or dissolved in appropriate solvents to make them soluble.

Since nanotubes vary by length and self-aggregate, they tend to form random piles of "spaghetti". Once in a tangled matte they can only be used in plate form arrays; for example, as a conductive plate in capacitors, a tangled matte of nanotubes is separated by a dielectric and can be rolled or stacked plate formed into a capacitor.

SUMMARY OF THE EMBODIMENTS

For descriptive purposes of this disclosure, the example nanotube described is the single wall carbon nanotube in its simplest form, the "arm chair" form. The other forms are the "zig-zag" form and "chiral" spiraling form. Each of these geometrically described nanotube structures carry electrons in a different manner and have unique but different electronic and mechanical properties. The "arm chair" form which is a regular hexagonal "chicken wire" carbon type nanotube is an excellent electric conductor. Other forms and types of tubes have different Fermi points, and are more semiconducting then the arm chair form. The arm chair form would be used where ordinary copper wire would be used, or field emission is desired. The other forms, namely zig-zag and chiral forms can be substituted where unique semiconducting properties of the device with specific Fermi states are desired.

Different chemical nanotubes possess distinct properties. For example, a boron nitride nanotube's electrical properties are less dependent on their geometry, size, and diameter than a carbon nanotube's properties would be. These different chemical types of nanotubes have different properties and these can be further exploited.

Carbon nanotubes have high tensile strength, but are not brittle. Nicely flexible, carbon nanotubes can be made to oscillate at their resonant frequency without breaking easily. At room temperature they vibrate and whip around under the effects of Brownian motion. These movements can be exploited to assist in the formation of regular arrays by propulsion into hydrophobic guidance channels. Carbon nanotubes conduct heat better than diamonds and depending on how they are configured and oriented, conduct electrical amperages better then copper.

Carbon nanotubes that can be spaced precisely can be used in a manner similar to "micro-electron guns" and arranged just as in old-fashioned cathode ray tubes; to fire electrons to excite phosphors to emit light at low voltages. If these thin metal films are used instead of phosphors these nano-scale cathode ray tubes can be used to emit X-rays. Light emitting phosphor arrays and X-ray devices take advantage of the carbon nanotube's inherent stability allowing them to emit more light and not burn out as rapidly as conventional molybdenum electrodes, extending the service life of a display. Carbon nanotubes can be manufactured with functional derivative groups such as but not limited to —COOH, —NH$_2$, —CN, —SH. Other groups may include, but are not limited to: halo, C$_{1-6}$alkyl, CN, haloC$_{1-6}$alkyl, OH, O—C$_{1-6}$alkyl, phenyl, naphthyl, indolyl, imidazolyl, pyrazolyl, pyrimidinyl and O-phenyl, said phenyl, naphthyl, indolyl, imidazolyl, pyrazolyl, pyrimidinyl and O-phenyl being optionally substituted with 1-3 groups selected from: halo, CN, OC$_{1-6}$alkyl, Ohalo C$_{1-6}$alkyl, CO$_2$C$_{1-6}$alkyl, CO$_2$H, C(O)C$_{1-6}$alkyl, SO$_2$C$_{1-6}$alkyl, NO$_2$, C(O)NR$^6$R$^7$ and pyrazolyl.

Applications for nanotubes include but are not limited to structural applications, electrical circuits, electrical cables and wires, batteries, solar cells, hydrogen storage, ultracapacitors, radar absorption, medical (for drug delivery, a scaffolds, for radio waves etc.), textile, and nanoelectromechanical systems.

Economic development of nanotube technology is limited given the difficulty in arranging nanotubes in precise arrays easily, repeatedly, and inexpensively. This disclosure teaches methods for formation of nanotubes and the nanotubes themselves, and applications of such through self-assembly into aligned arrays by the use of peptide engineering and DNA recombinant technology.

Barrel proteins are long amino-acid sequences (peptides) designed to fold into a barrel shape. These types of barrel proteins are most commonly found as porins, and usually reside within the lipid bilayer membranes of cells. They function as gates allowing certain molecules or ions, such as the potassium pore, to allow the transit of substances across the cell membrane between the internal cellular cytosol and external environment. These proteins come in three basic geometric arrangements, the simplest is the Up and Down Barrel Protein as shown in FIG. 1.

Barrel like structures with wider opening pores can be made of peptide sequences made of alpha helical bundles as compared in FIG. 2, but for their use in aligning nanotubes, the engineering of these structures is much more difficult than the beta-barrel "can" structure.

This disclosure teaches the use of the Green Fluorescent Protein model: the core of the barrel is quite hydrophobic and the exterior quite water soluble. In one embodiment, this disclosure teaches removing three amino-acid residues that make the aromatic fluorescent molecule at the center of the barrel and replacing them with hydrophobic and/or small non-polar or aromatic amino acids making the interior of the barrel much more polar.

The disclosure further teaches the arrangement of larger and smaller sized non-polar "R" groups on the barrels interior amino-acid peptide sequence can be a method for separating nanotubes based upon the their surface electron distributions. In other words, if higher concentrations of the "chiral" form of nanotube is required, the larger polar groups are arranged on the interior of the barrel in a spiral manner so the nanotube is rotated into the barrel, just like a screw being turned into a spiral channel made for it. Conversely, to produce the straight "arm-chair" form, the interior of the barrel has a straight arrangement or larger polar groups inline on the inside of the barrel.

The disclosure teaches finding these different barrels utilizing mutational cloning using random or site directed mutagenesis of their corresponding DNA sequences based either upon known structure, or through custom discovery by molecular evolution by those skilled in the art.

The Green Fluorescent Protein barrel, looking down the end-on view of the barrel, is reconstructed by altering the amino-acid residue sequence in the peptide. The diameter and circumference of the barrel is enlarged by adding an additional set of parallel and anti-parallel staves to the barrel. The length of the barrel is doubled or even tripled by copying the anti-parallel and parallel sequences and inserting them to make the staves longer as in any wooden barrel construction.

Green Fluorescent Protein (GFP) is known as the "Greek Key" barrel by the formation of peptides at the ends. While this "beta-barrel" protein functions to auto-catalytically form a fluorescent aromatic compound within its interior, it also excludes water from the interior of the barrel protecting the fluorescent aromatic compound. FIG. 5 leads to an example of an up and down beta barrel pore protein. Inspection of the FIG. 5 schematic reveals the parallel and anti-parallel map of a simple up and down barrel with eight (8) staves. Adding them end to end upon each other doubles the length of the barrel. Adding more staves in the middle of the barrel makes the diameter of the barrel larger, and also opens up the center opening core of the barrel.

Testing is performed using in vitro 5' capped synthetic mRNA or creating plasmid DNA sequences and using bacterial fermentation and protein isolation to optimize their production. These proteins tend to self assemble and are most stable in their beta Barrel configuration.

The GFP barrel has properties that are ideal for self-assembly. An entire peptide can be left out of the barrel and added later to restore the chemical function and integrity of the barrel.

The GFP barrel's amino-N and carboxy-C terminal ends are ideal for adding small peptide ligands like such as a small 14 amino acid "biotinylation" lysine tag so that a specific end of the barrel can be tagged in a very precise and easily repeated way that would be in the exact same place on all such molecules; or synthesized directly onto all the empty GFP barrels. In this case: the biotinylation site, placement on an Avidin coated surface is well known to those practiced in the art. The resulting surface contains in a precise up and down orientation, the barrel on a substrate matrix such as Avidin or Stepavidin. Conversely, Streptavidin or Avidin amino acid sequences are cloned into the s-barrel at the N or C terminals, or via linking peptides, incorporated directly into one of the up-down looping regions.

Avidin type molecules are spotted in very precise nano-arrays; the synthetic GFP barrels (herein known as s-barrels) bond to those surfaces very strongly, and if the nanotubes are long enough the nanotube will remain flush against the Avidinized bonding surface and remain inside the barrel.

Placing the entire array as described in the preceding paragraph in high ionic strength aqueous solution results in the nanotubes, if nonpolar, driven down into the tube to seek shelter into the more hydrophobic environment of the s-barrel interior as favored energetically.

Spotting the Avidin surface around an independently wired gold pin or cup that the nanotube contacts, forms an electrical connection, since Avidin can be spotted in a specific location near or around the gold pin, or on the side of a gold "cup." The disclosure teaches many surfaces: hydrophobic surfaces such as diamond, graphene, carbon elements, or even flat matts of tangled nanotube meshes are spotted with Avidin, and arrays of s-barrel arrays, each containing a nanotubes, are made and positioned easily.

The s-barrel's water soluble polar exterior and hydrophilic peptide composition allows placement of precise chemical ligands repeatedly in precise locations on the outside (or inside) of the barrel.

The disclosure further teaches incorporating natural occurring or synthetic amino acids on or in the barrel during s-barrel in vitro protein synthesis. Customized tRNA with synthetic amino-acid chemical moiety in the growing polypeptide chain is well known to those in the art. Specific chemical ligands are accomplished and reliably repeated in exact spatial orientation on all the s-barrels during fermentation or in vitro protein synthesis manufacture.

Specialized chemical ligands are desired to alter the orientation of s-barrels in 3D space, are made using a DNA template corresponding to the s-barrel peptide sequence containing a synthetic amino-acid residue. Using specialized artificial or substituted anticodons in the template DNA enables the design barrels to form stable and rigid chemical bonds between themselves, orienting correctly, and simultaneously in large planar arrays to develop sorting tools for nanotubes and as holders for nanotubes.

One alignment method is to loop a biotinylation lysine extending from the exterior of the barrel; biotinylation using an enzyme such as BirA made in vitro. Using an Alkyne on the N or C terminal of the peptide, the end of the barrel is fixed oriented properly in the vertical z-axis position and Avidin or Streptavidin is then added to make a cross-linked array between s-barrels in the x-axis direction. These are guided by placing carboxyl groups across from lysine or arginine residues on the y-axis to form a self assembling array of spaced s-barrels.

Once layered on a substrate in a monolayer, a native GFP barrel's nonpolar hydrophobic interior is used like a temporary or permanent jig for alignment and sorting tool, allowing only nanotubes of the a smallest diameter to enter the interior, forced into the centers by fleeing an increasing ionic environment. The hydrophobic nanotubes seek refuge from an increasing ionic strength aqueous environment deep into the interior of the non-polar lining of the s-barrel or huddled together to escape the polar environment. This allows for isolating individual nanotubes and moving nanotubes into the spatial arrangement pre-arranged by the s-barrel protein positions.

Another method of spacing nanotubes is using viral self assembling viral coat and lambda phage tail proteins. These proteins have hollow diameter inner cores that can be used to guide vapor deposition nanotube growth in precise arrays.

The disclosure teaches a protein used as a molding tool to form an aerogel casting of that protein. The disclosure teaches an array of identical proteins forming a molding tool to form an aerogel casting of the array of identical proteins. The disclosure teaches the protein is a protein made up of individual peptide subunit proteins that self-assemble into a larger protein. The disclosure teaches the protein is a barrel protein, a vault protein or a tubular protein. In one embodiment, the protein is a viral or phage protein. In one embodiment, the protein is a flagellar protein. In one embodiment, the protein is an extended barrel protein made by doubling, tripling, or quadrupling the length of the parallel and antiparallel peptides that form the structural staves of the barrel protein. In one embodiment, the protein forms a widened diameter barrel protein made by adding more staves to the barrel by the addition of parallel and antiparallel peptides and in and out loop sequences that form the structural circumferential staves of the barrel protein. In one embodiment, the protein comprising chemically altered ligands wherein said ligands insure the protein is oriented in only one way within an x-y-z coordinate. In one embodiment, the protein comprises a fusion protein of luciferase wherein the luciferace oxidizes a Coelenterazine analog to produce light of a wavelength between 395-415 nanometers.

In one embodiment, the aerogel casting is made using a silicon oxide polymeric forming soluble gel. In one embodiment, the aerogel casting is chosen to form an aerogel that is hydrophobic. In one embodiment, the aerogel casting uses supercritical carbon dioxide to retain its structural physical geometry once dried or rewetted. In one embodiment, the casting is used as a template to form nanotubes deposited and grown by vapor deposition methods. In one embodiment, in the nanotubes grown, all atoms of Hydrogen used during their vapor deposition manufacture are replaced with Deuterium. In one embodiment, in the nanotubes grown, all atoms of Hydrogen used during their vapor deposition manufacture are replaced with Tritium. In one embodiment, the dried aerogel comprises spherical Fullerenes deposited within the aerogel matrix.

In one embodiment, the disclosure teaches a method for making nanotubes comprising using barrel proteins acting as scaffolds to guide assembly of nanotubes. In one embodiment, the disclosure teaches a method for producing stable arrays of nanotubes comprising using nano-molecular modling jigs to format nanotubes into stable arrays with precise geometric architecture. In one embodiment, the disclosure teaches a method for producing nanotubes comprising using highly modified barrel proteins to form hydrophobic and hydrophilic channels that guide the nanotubes into the barrel centers, or other geometric patterns utilizing silicone aerogel to form nano-molecular molds, jigs, and surfaces to position nanotubes in precise geometric arrangements and arrays.

In one embodiment, the disclosure teaches a nanometer scaled device made by the process of using barrel proteins as self-assembling molding tools. In one embodiment, the disclosure teaches a device, wherein the protein is a modified GFP protein. In one embodiment, the disclosure teaches a polyvalent nanoparticle produced by the process of using building blocks wherein the building blocks comprise barrel proteins as a scaffold. In one embodiment, the disclosure teaches a method of making a nano structure, comprising making an array of identical proteins, forming a molding tool to form an aerogel and casting of the array of identical proteins. In one embodiment, the disclosure teaches the method for forming an aerogel casting of a protein comprising using that protein as a molding tool. In one embodiment, the disclosure teaches the method wherein the aerogel casting comprises an array of identical protein. In one embodiment, the disclosure teaches a method wherein the protein comprises individual peptide subunit proteins that self-assemble into a larger protein.

BRIEF DESCRIPTION OF THE DRAWINGS

FIG. 7 shows addition of FIG. 5 and FIG. 6 doubles the length of the barrel (fragments of SEQ ID NOs: 1-8).

Remove photoresist mask.

Figure 23:
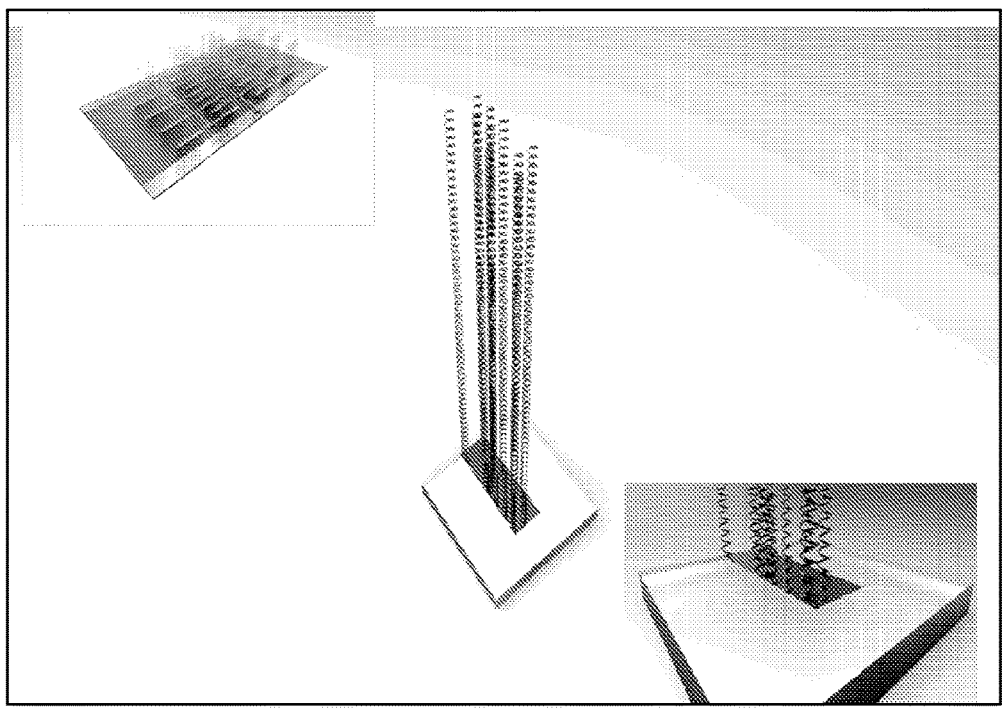
Figure 24:
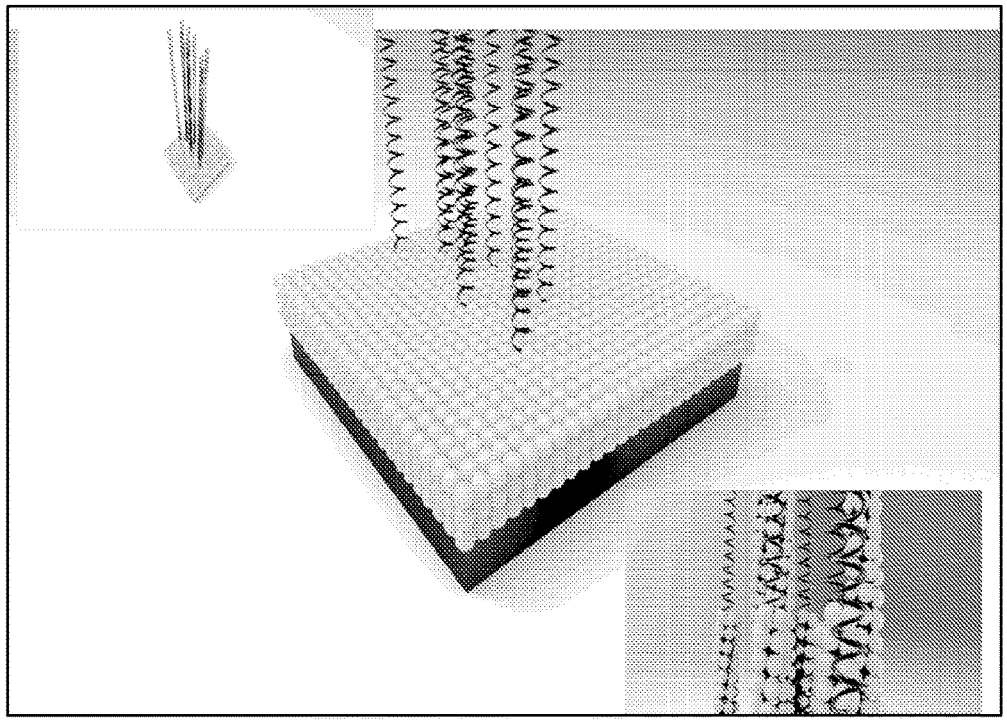
Figure 25:
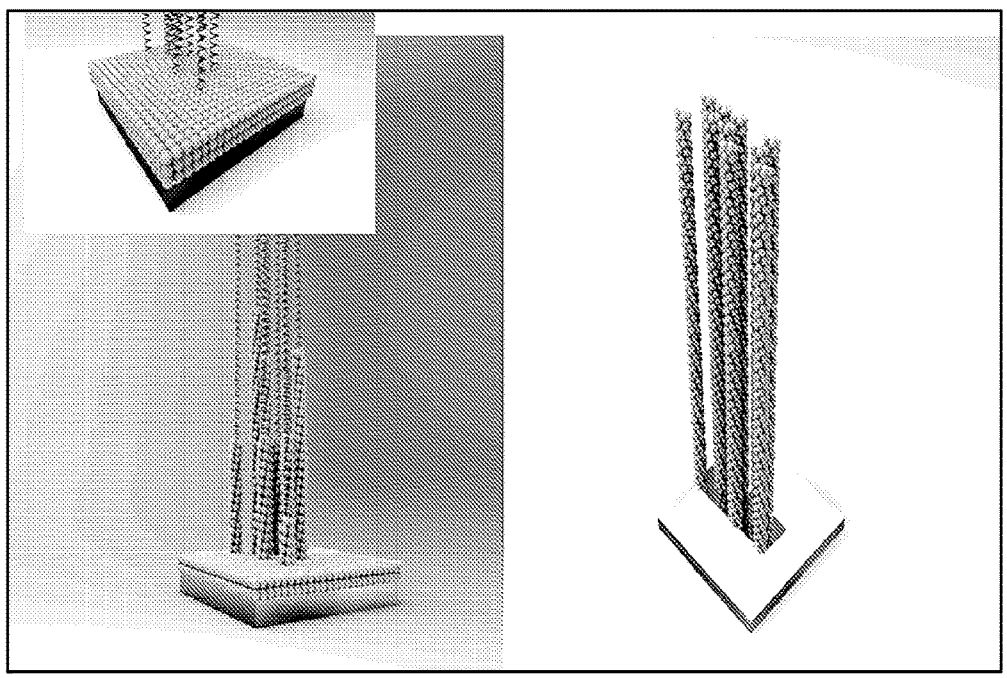
Figure 26:
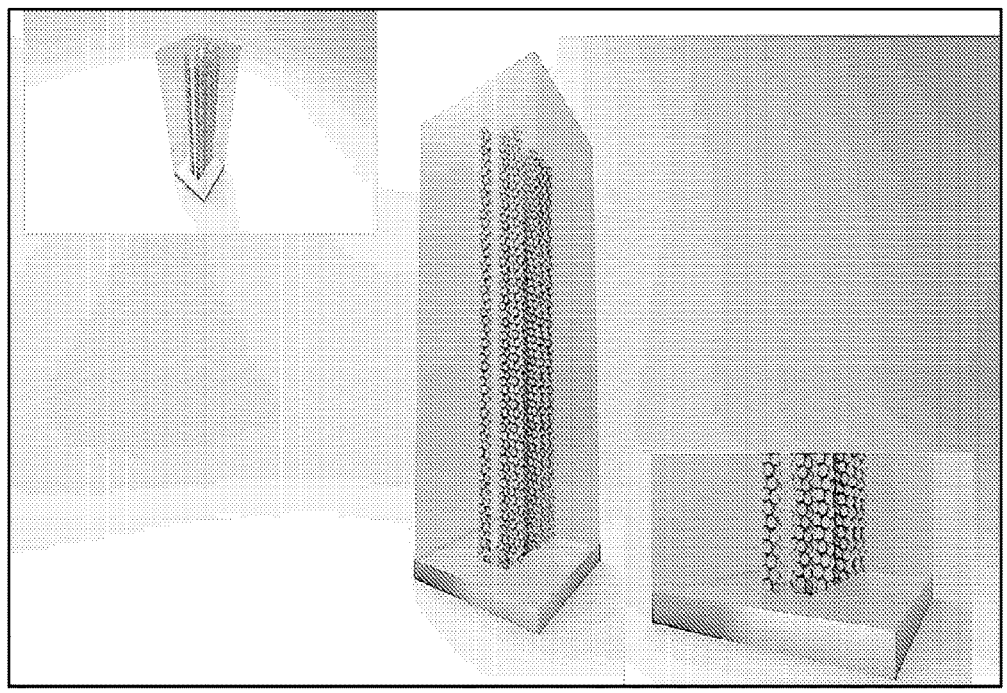
Figure 27:
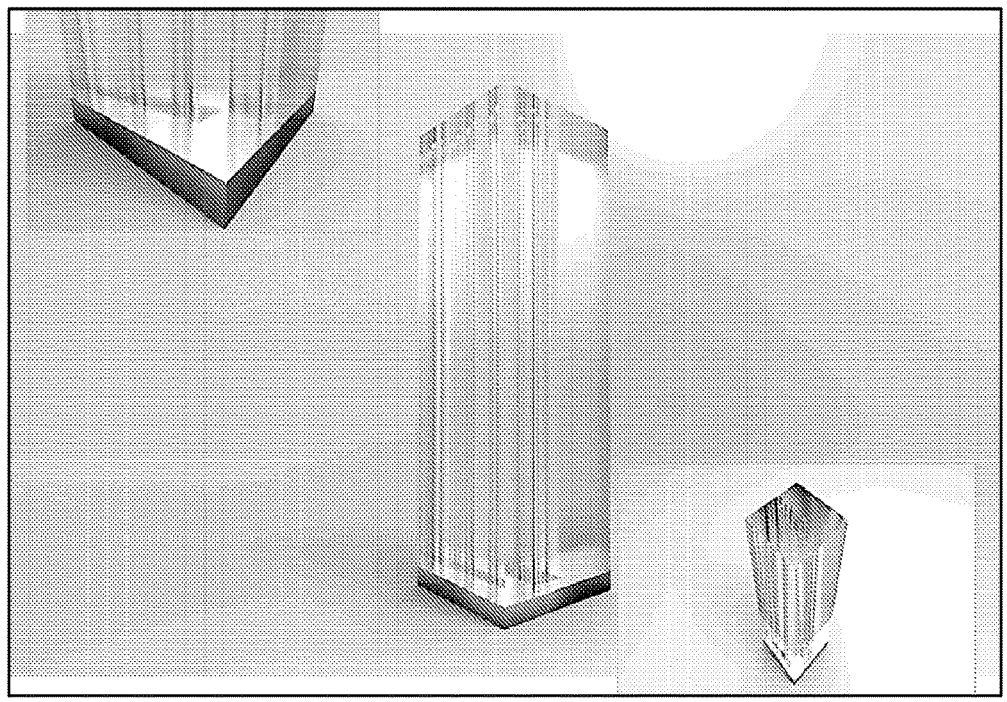
Figure 28:
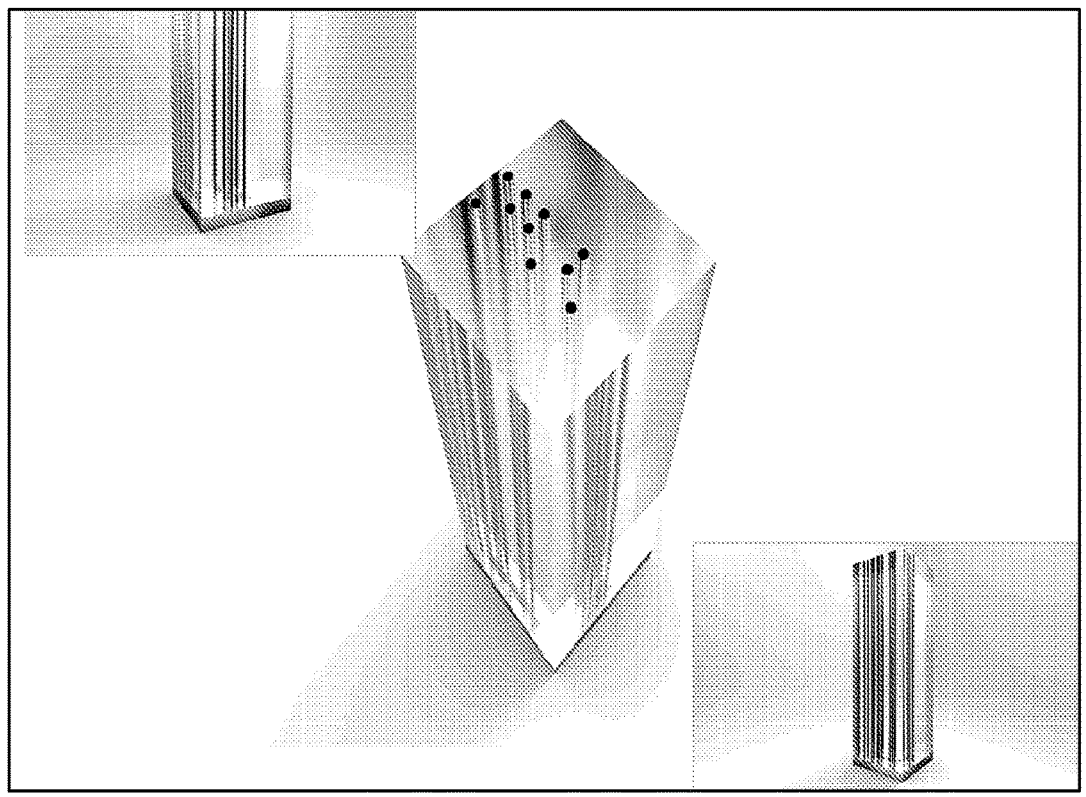
Figure 29:
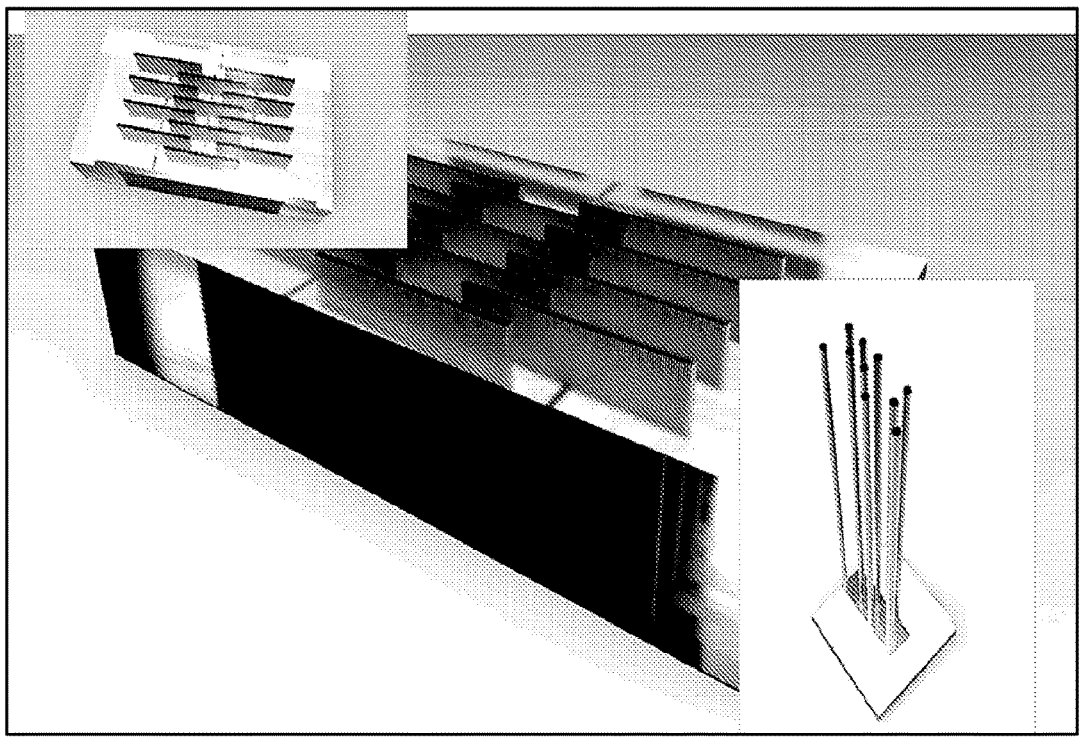
Figure 30:
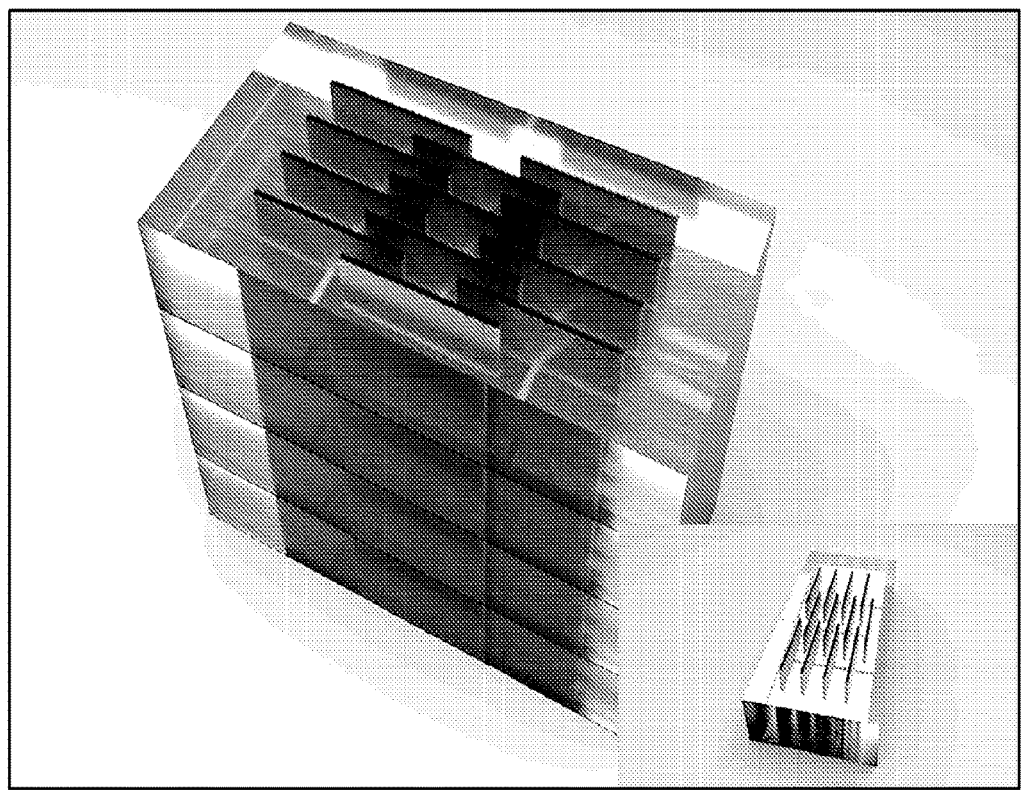
Figure 31:
Figure 32:
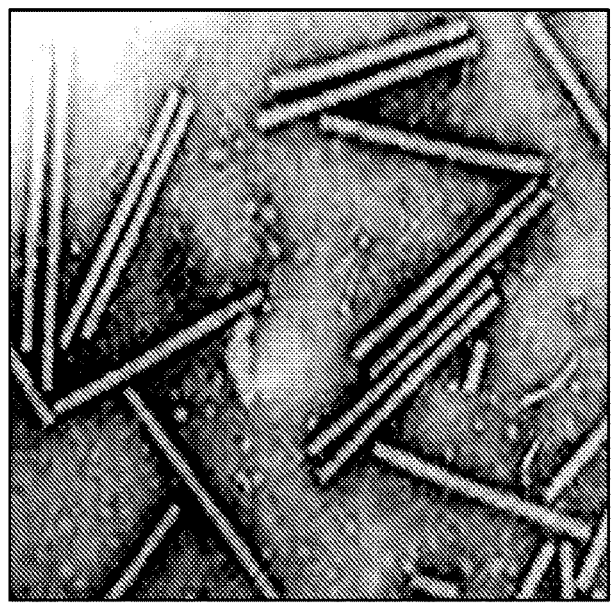
Figure 33:
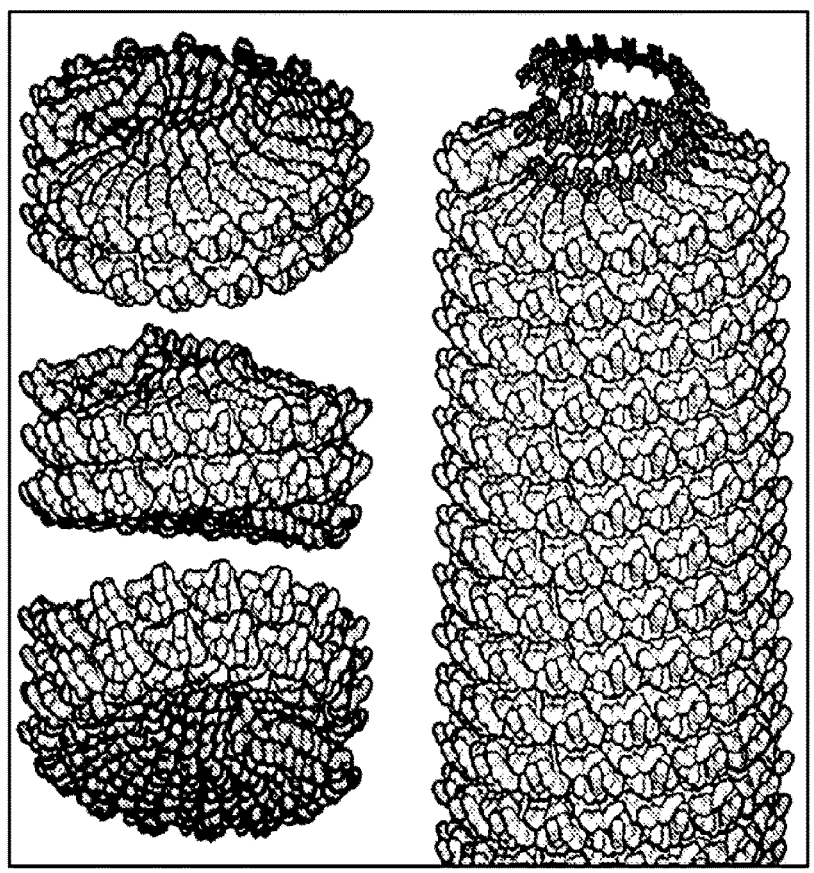

FIG. 23 shows Add TMV RNA—Add TMV RNA and allow to bond with the aid of FeNO3 medium.

FIG. 24 shows Add Protein Monomers—Add protein monomers to begin growth of TMV Rods. Proteins begin growth up each RNA strand.

FIG. 25 shows Growth of full TMV Rods—Protein monomers added. Protein monomers begin to adhere to TMV RNA. TMV Rods fully grown.

FIG. 26 shows Add Silica gel-sol—Silica gel-sol is added.

FIG. 27 shows Digest out TMV Rods—Digest both the TMV Rods and RNA from the silica gel-sol leaving a mould recess. Gel-sol is dried in Methanol and CO2 liquid to form Aerogel with tubular cavities containing Fe catalyst on bottom.

FIG. 28 shows Grow Nano-Tubes—Grow Nano-Tubes via vapor disposition.

Nano Tubes grow in support mould created by digesting the protein monomers and RNA from Silica gel-sol.

FIG. 29 shows Panel completion ready for application—Fully formed Nano Tubes stand suspended in dried Aero-gel insulating dielectric material.

FIG. 30 shows Stack panels to form battery assembly—Individual plates are stacked to form high density capacitor type rapidly charging battery assembly.

FIG. 31 shows Nano-Tube spaghetti

FIG. 32 shows Rods

FIG. 33 shows Rod Assembly

DETAILED DESCRIPTION

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

EXAMPLES

The following examples are provided for illustrative purposes only and are not intended to limit the scope of the invention.

Example 1

Capacitor:

Traditional electronic silicon wafer mask technology is used to create a pattern of 600 nm thick by 30-100 nm wide layers of aluminum, copper, nickel, titanium or titanium aluminum or iron patterns. Here we are chose a gold wiring array in an inter-digitating pattern to create for example a capacitor. Alternating positive and negative areas are equally spaced and separated by a 20-50 nm pitch nonconductive areas. The grid and branch design would each terminate on a 100 nm wide×600-1,000 nm thick gold bar positive connector and similar negative ground bar at opposing ends of the capacitor array surface. This described structure is referred to as an array-plate.

The array-plate is spin-coated with an ethanolic solution of 20-50 mM Ferric Nitrate or Ferric Chloride solution containing 5-20% nitrocellulose and allowed to dry in a vacuum. Concentrations of Ferric Nitrate or Ferric Chloride catalyst (growth seeds) can vary depending upon the density of nanotubes desired. Another example, Cobalt or Nickel solutions can be used in place of Ferric Nitrate catalyst solutions if multi-walled carbon nanotubes are desired. Changing the catalyst, in this case Ferric Nitrate to a different catalyst is a likely embodiment applied to different patterned arrays and for different electronic or structural purposes, such as field emission in x-ray or phosphorus display screens.

Tobacco Mosaic Virus (TMV) antisense 20-60 oligomers designed to anneal by complimentary bonding to the 3'end of the TMV-RNA is arrayed onto the nitrocellulose by direct micro-piezo heads ejecting, lithographic printing, or micro-lithographic stamp printing TMV-RNA solutions using arrays made by photolithography on polydimethylsiloxane stamps cured in oxygen plasma.

Another linkage method is to silanate the oxide with amino-propyl triethoxysilane which then allows a free primary amine available for bonding which we can use as a handle of sorts. We can chemically activate the amine to a nitrophenyl carbamate which reacts with a specially designed amine linker on the DNA or RNA oligomers, or to a special amine group synthesized directly on the TMV RNA.

Figure 1:
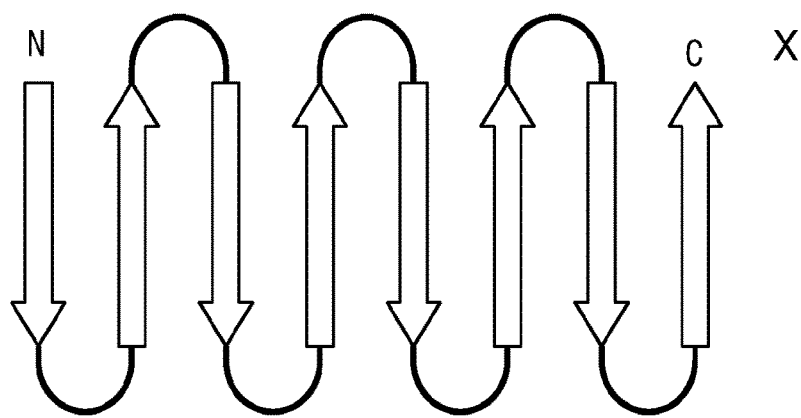
FIG. 1 is a barrel protein with the specific properties for self-folding, length, width, hydrophobic non-polar nature of the interior, water solubility of the exterior, and derivitization of the exterior at both ends and sides of the barrel so they are covalently linked to a substrate and to each other in a very precise spatial array.
Figure 1:
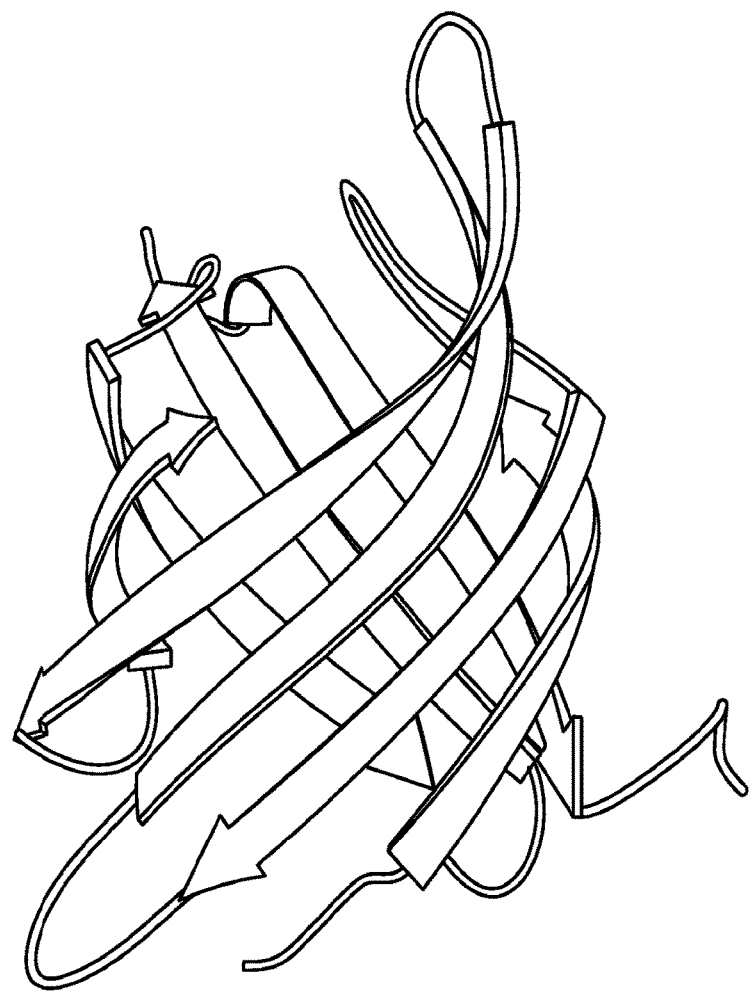
Figure 2:
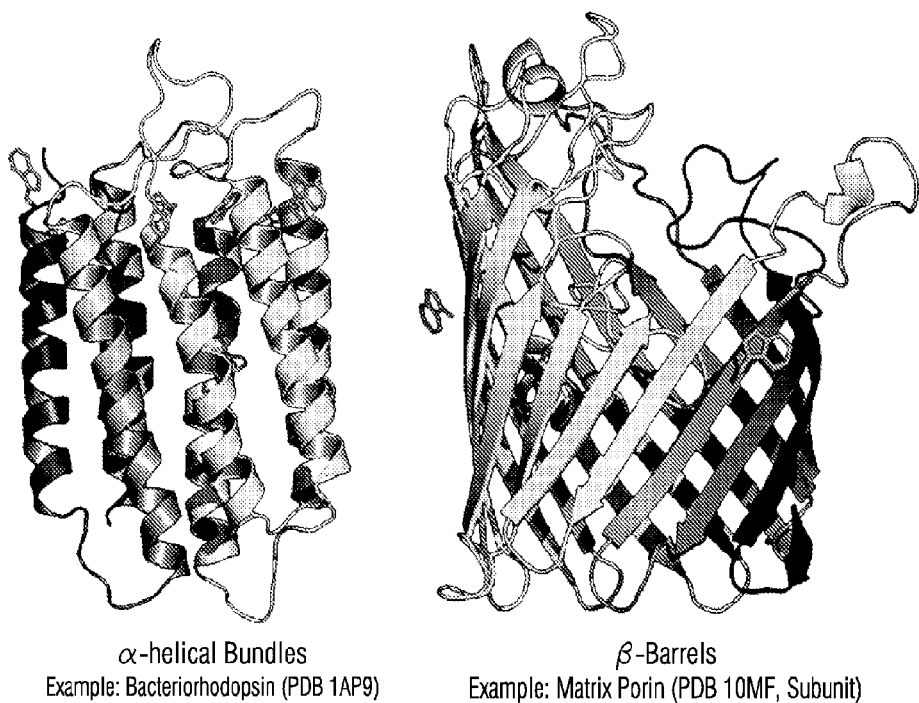
FIG. 2 shows barrel like structures with wider opening pores made of peptide sequences made of alpha helical bundles.
Figure 3:
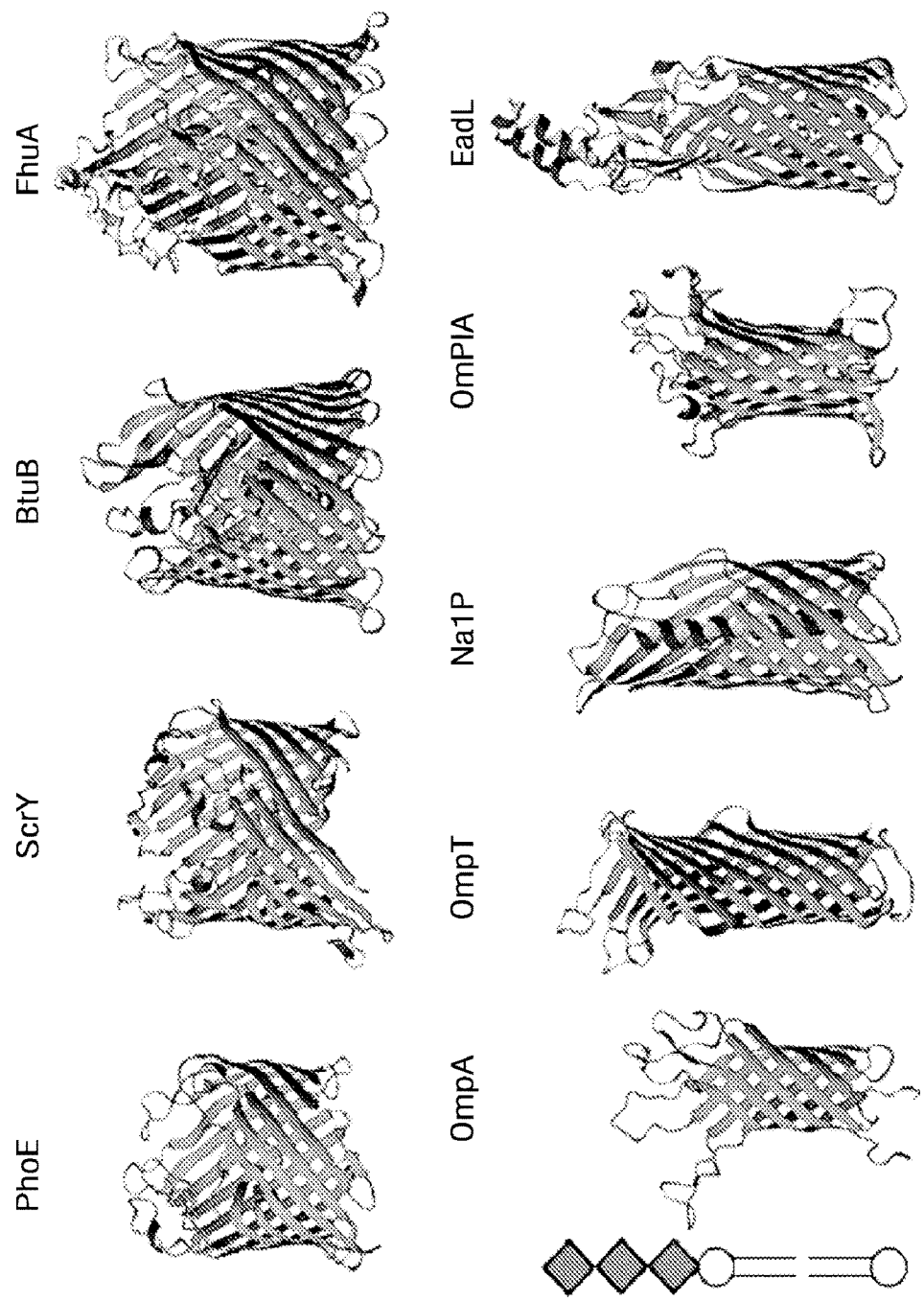
FIG. 3 shows barrel proteins are peptides that have hydrophobic exteriors enabling them to reside stably within the lipid membrane. They also have functional interiors that are designed for a particular function such as transport of a molecule inside or out of a cell.
Figure 4:
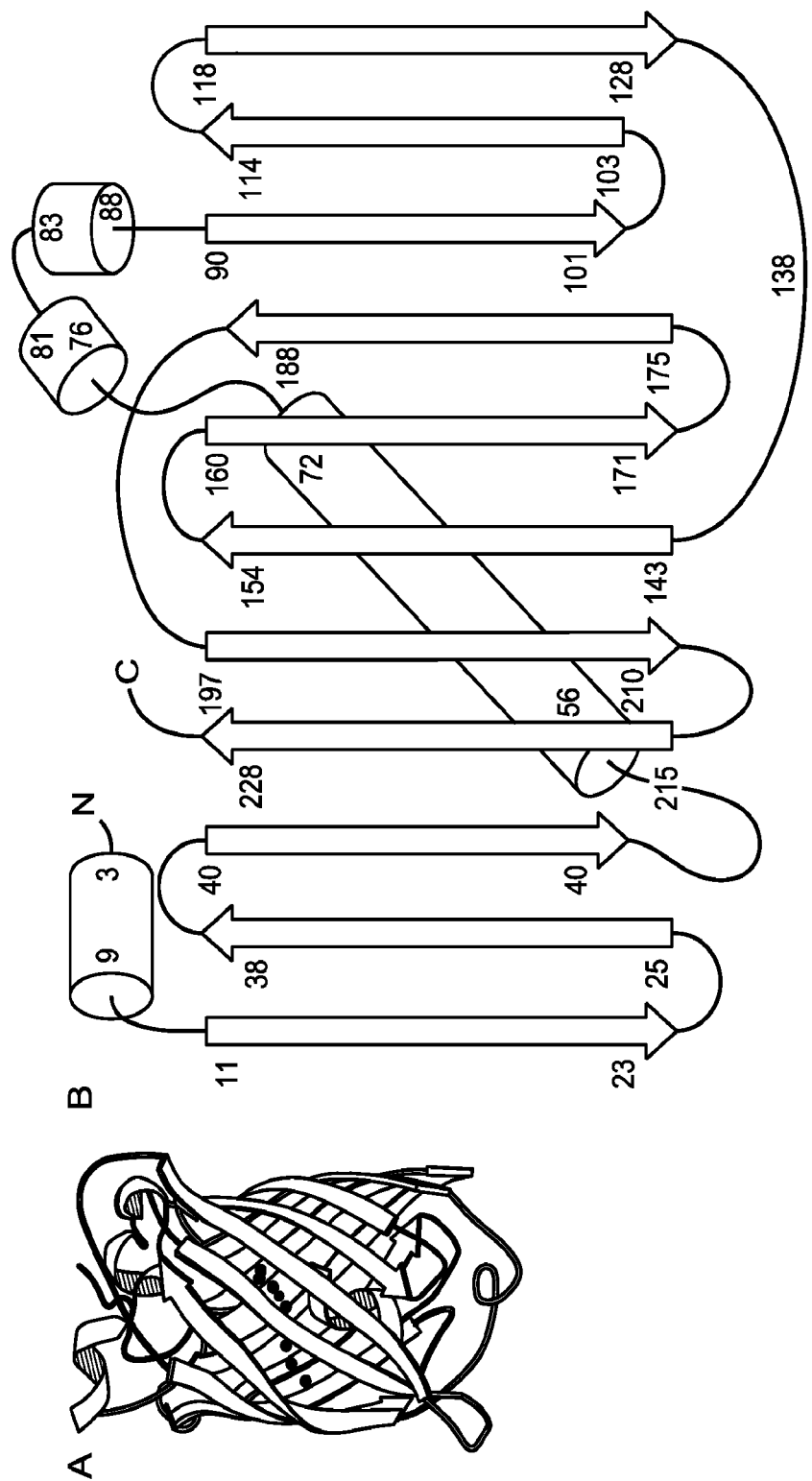
FIG. 4(a) is a schematic drawing of the backbone of GFP produced by the program MOLSCRIPT (32). The chromophore is shown as a ball and stick model.
FIG. 4(b) is a schematic drawing of the overall fold of GFP. Approximate residue numbers mark the beginning and ending of the secondary structure elements. N, $NH_2$-terminus; C, COOH-terminus *SCIENCE*: Vol. 273 (1996).
Figure 5:
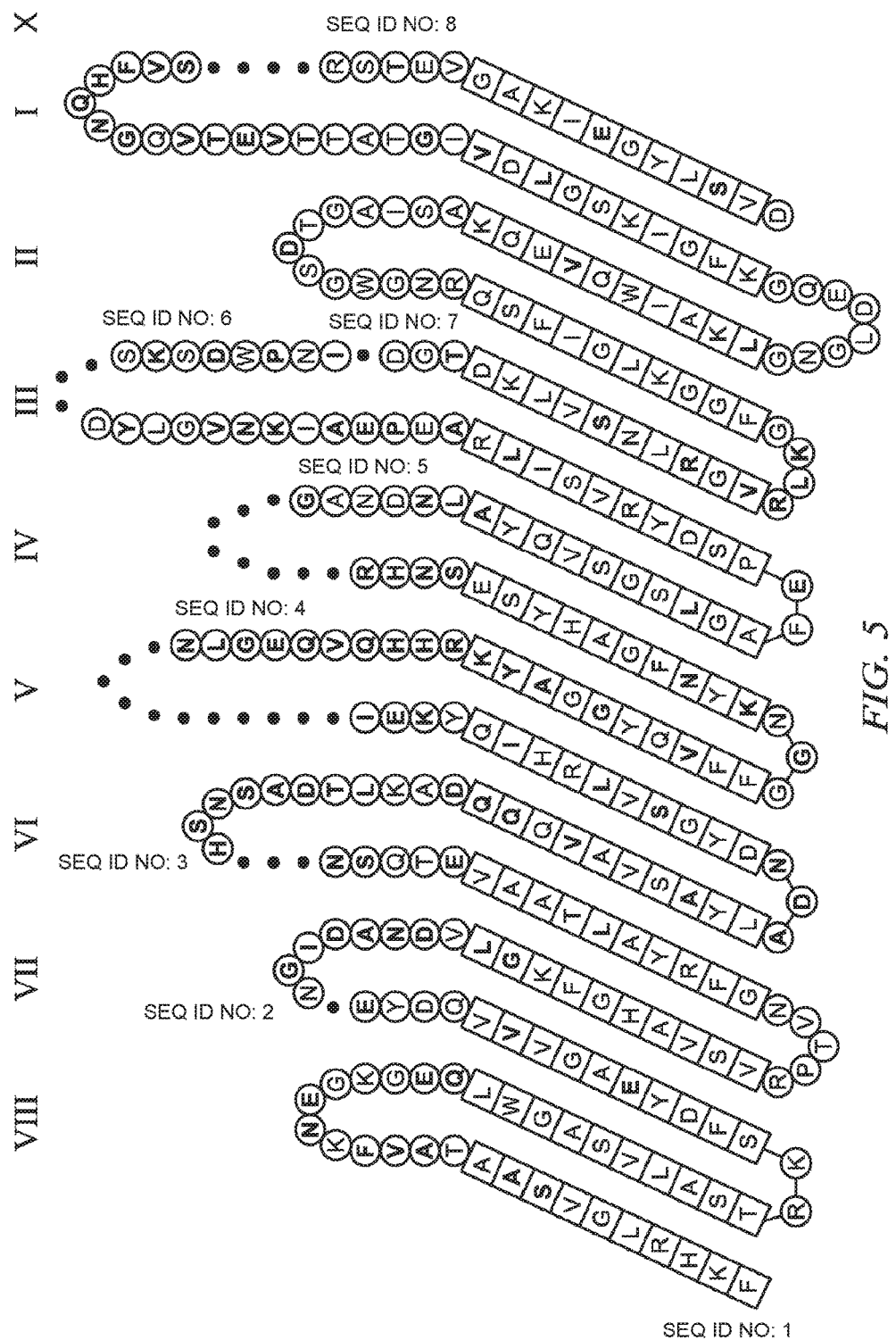
FIG. 5 reveals the parallel and anti-parallel map of a simple up and down barrel with eight (8) staves (SEQ ID NOs: 1-8).
Figure 6:
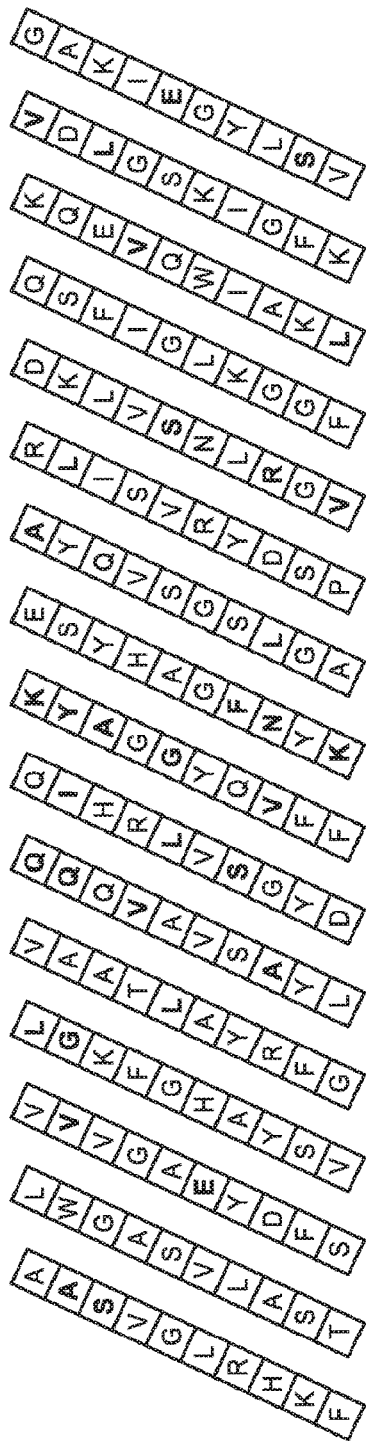
FIG. 6 is a copy of just the stave section of the protein in FIG. 5 (fragments of SEQ ID NOs: 1-5, 7, and 8).
Figure 8:
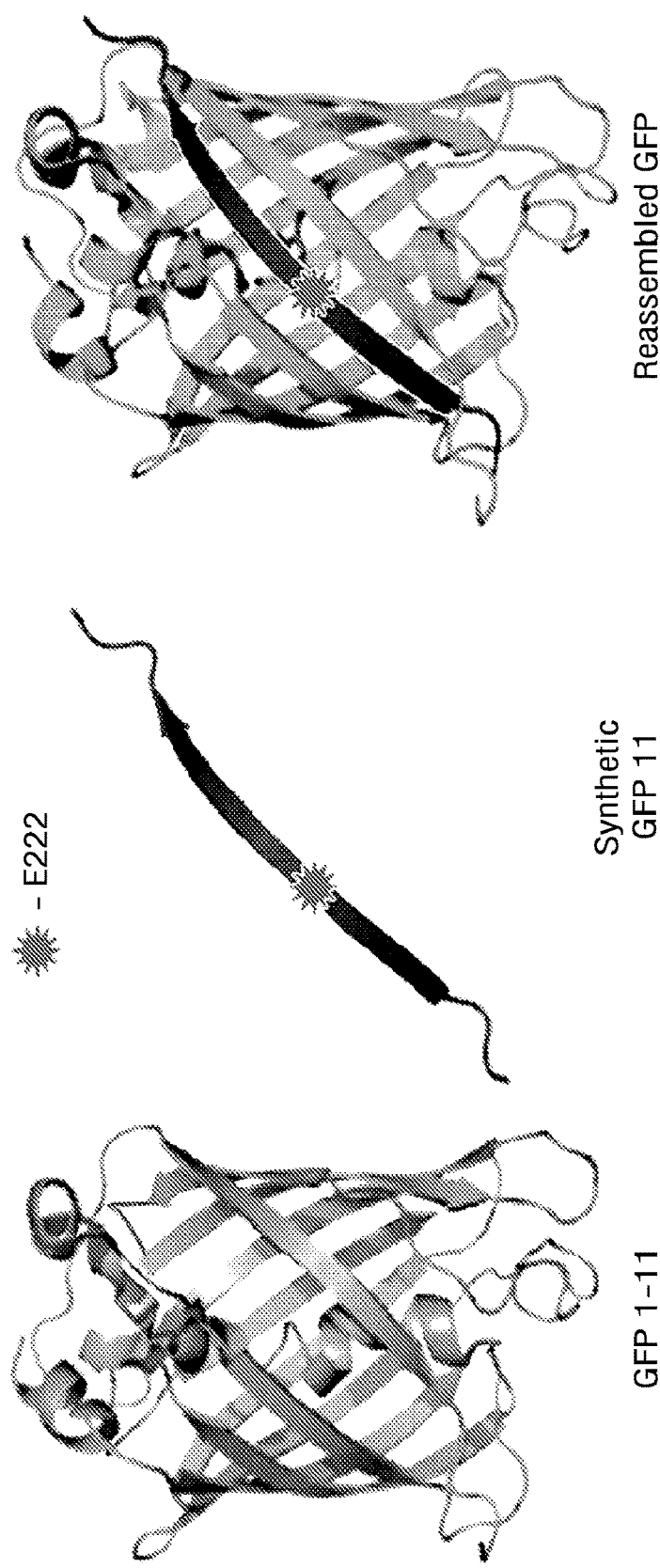
FIG. 8 shows that the GFP barrel has properties that are ideal for self-assembly. An entire peptide can be left out of the barrel and added later to restore the chemical function and integrity of the barrel.
Figure 9:
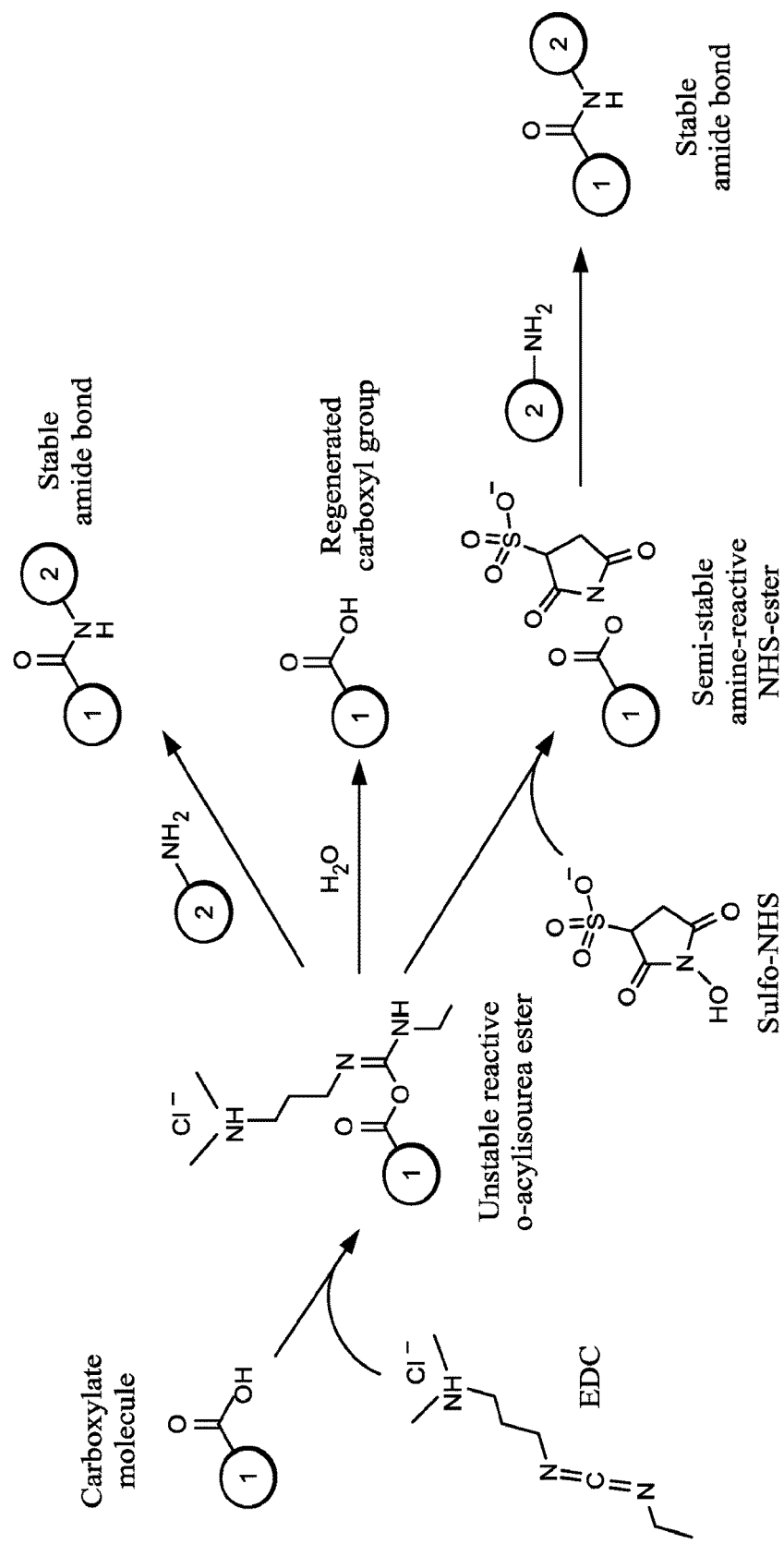
FIG. 9 shows arrays that are printed in a pattern and alignment corresponding to the gold wiring lying directly underneath (below the nitrocellulose layer).

Using a carboxy-cellulose instead of nitrocellulose and activate with EDC/NHS to create an active ester is also contemplated herein. Synthesize the DNA with an amine linker on the 5'-end which will then form a covalent bond fairly specifically, such as shown in FIG. 9: EDC/NHS Linkage chemistry.

These arrays are printed in a pattern and alignment corresponding to the gold wiring lying directly underneath (below the nitrocellulose layer). The oligomer's length mentioned in this embodiment has to be determined empirically, if too short they may not bond well to the nitrocellulose, too long and the TMV protein coat subunits will not grow well to form a horizontal baseplate fixed to the nitrocellulose layer. The right length can be determined empirically by TEM or SEM microscopy after the TMV coat proteins are applied and grown into tubes, whose axis should lay perpendicular to the wafer surface. This will have to be determined empirically for any self-assembling macromolecular complex, be they viral proteins, tubulin, flagellin, polylysine, or other self-polymerizing organic complex.

For TMV coat protein, the array-plate is placed in an oven at 80 C. for 2 hours to bond the DNA antisense oligomers to the nitrocellulose as is the ordinary technique for making to those skilled in nucleic chemistry, hence creating the first step of a Southern Blot.

Single stranded genomic sense TMV-RNA made with the 16-60 mer complimentary bonding region located on the 3' end of the TMV-RNA is applied in excess by flooding the array-plate with purified single stranded TMV-RNA in suitable buffer as used in Southern Blotting of nucleotide sequences, and allowed to anneal from slightly above the predicted melting temperature (DNA-RNA) and cooled gradually to facilitate DNA-RNA hybridization.

The array-plate is then washed in buffer to remove any unbound free TMV-RNA. A concentrated solution of partially purified Tobacco Mosaic Virus coat protein subunits of (M.W. 158) is flooded onto the array-plate in buffered physiologic saline containing 20 mM calcium chloride. The array-plate is then incubated for two to three hours at 20-35 C. to allow the TMV coat proteins time to self-assemble into tubes around the 5' end of TMV-RNA in suspended solution above the array-plate.

Should more precise arrays be desired, an electric field can be placed across the gold contact bars to a gold or gel-buffer agar plate held above in contact with the TMV coat protein solution to create an "electrophoretic field" in the solution that will force the TMV rods more perpendicular to the array-plate surface.

Naturally occurring TMV rods form a rigid thermo-stable structural rod of 300 nm in length. The inner-diameter is 6 nm containing a 4 nm hollow inner channel, the single strand TMV-RNA occupies 2 nm of the inner diameter. By cloning a hexa-histidine (his-tag) on the carboxyl terminus of the TMV coat protein, lengths can be increased to as long as 1,200 nm by stacking in acidic conditions. The his-tagged TMV coat proteins will self-stack and assemble without the RNA template.

Figure 10:
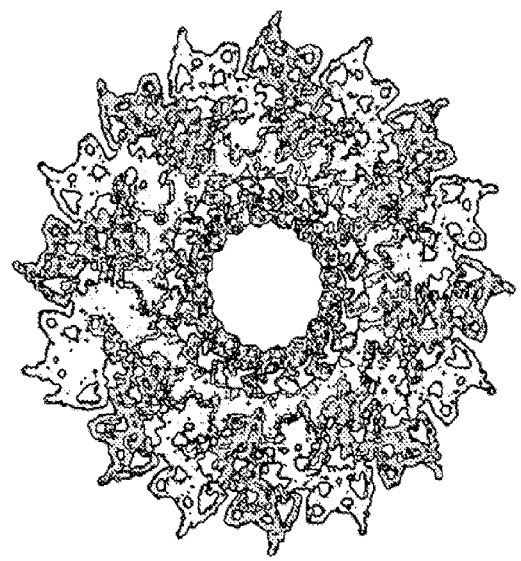
FIG. 10 shows a cross section of the partially assembled TMV coat protein nanostructure with an inside open core (hole down the center) of 4 nm diameter.

FIG. 10 show a cross section of the partially assembled TMV coat protein nanostructure with an inside open core (hole down the center) of 4 nm diameter.

Figure 11:
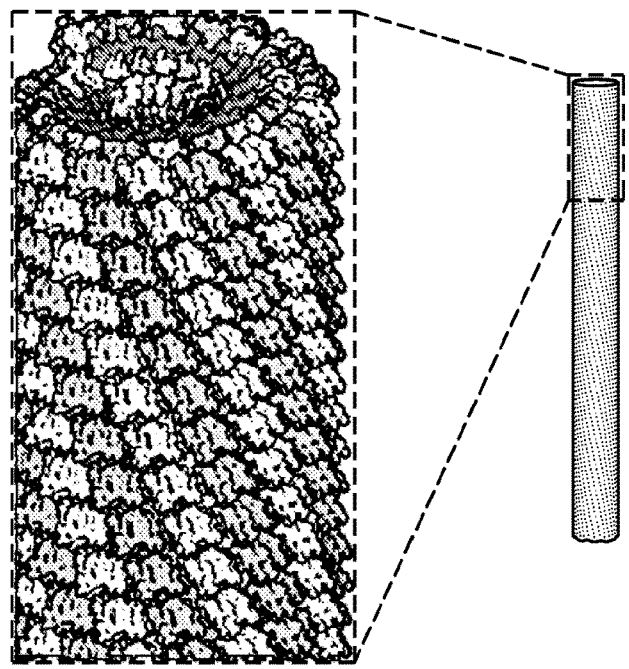
FIG. 11 shows the completely assembled tubular structure that is 18 nm in diameter and 300 nm in length.

FIG. 11 shows the completely assembled tubular structure that is 18 nm in diameter and 300 nm in length.

Once assembled the completed TMV rods are gently washed with 5-10 volumes of distilled water pH 7 containing 20 mM calcium chloride (to prevent disassembly of the coat proteins once assembled) removing any unbound coat proteins and ss-TMV-RNA molecules.

An aerogel rigid support (silicon casting) of the whole TMV array is performed by creating a sol-gel of tetramethyl orthosilicate (TMOS, $Si(OCH_3)_4$), and/or tetraethyl orthosilicate (TEOS, $Si(OCH_2CH_3)_4$) or by using pre-polymerized Silbond H-5 mixed with small amount of ammonia hydroxide adjusted to pH 7.8-8.2 overnight in order to catalyze the formation of a silicon dioxide gel-sol around the TMV coat proteins.

Carefully raising the pH by the adding stronger ammonium solutions or introduction of ammonia gas over the surface solution to raise the pH (to catalyze the sol-gel TMOS polymerization) is required to prevent the TMV coat proteins from disassembly if the pH is raised too rapidly.

For this example the TMOS (sol-gel) is spin coated to a height of 280-290 nm, leaving the ends of the TMV coats rising above the TMOS surface level, by making the spin coating very thin in layers, sol-gel TMOS aqueous starting materials can be prevented from entering the inner core opening of the TMV particles.

If desired, spin coating the TEOS sol-gel in a partial vacuum and flooding the array-plate above the surface of the TMV particles followed by brief low energy momentary sonication, followed by vacuum de-bubbling, using higher ethanol concentrations in the mixture of TMOS will disperse the TES and make an even distribution of sol-gel forming within the 4 nm diameter core of the TMV particle array.

Micro air bubbles and any entrapped air can be removed by vacuum of the array before the TMOS solution is applied, or by degassing under a vacuum after the TMOS solution is applied or spin coated. Small bubbles are avoided by increasing the concentration of ethanol mixed in the TMOS sol-gel mixture, but not enough ethanol to denature the TMV proteins, or other protein arrays is used.

The soft newly formed polymerizing sol-gel silicon-oxide matrix is allowed to firm and harden over 48-72 hours, aided by gradually increasing the pH by diffusion of ammonia gas into the sol-gel phase of TMOS or TEOS. Raising pH catalyzes complete consumption of TMOS monomers during polymerization of the silicon-oxide surrounding matrix and time stabilizes the entire array-plate sol-gel structure.

Recipes vary from one part or to two part silicon polymerizations, for a simple one-part recipe 50 mL of TEOS, 40 mL of Ethanol is made. A solution containing 35 mL of ethanol, 70 mL of water, 0.275 mL of 30% aqueous ammonia, and 1.21 mL of 0.5 M ammonium fluoride are gently mixed and this solution is poured in a thin layer onto the TMV coat array-plate.

A denser and finer polymerization is produced with a solution containing 35 mL of ethanol, 75 mL of water, and 0.35 mL of 30% aqueous ammonia which is gently added to a 50/50 mixture of pre-condensed Silbond-H5 by mixing gently and pouring onto the TMV protein array and allowed to harden over 36-48 hours.

Proteins that are unstable in alkaline environments can be used with TMOS and TEOS like ingredients that are catalyzed by acid conditions as well.

Hydrophobic properties can be imparted to the final aerogel gel-sol product by incorporating mixtures of organosilanes such as methyl-, ethyl-, and or propyl-trimethoxysilanes. Making these aerogels in a two-step acid-base catalyzed process using N,N,N dimethylformamide and TEOS, isopropanol mixture along with trimethyl-chlorosilane/heptane combinations are well known to those skilled in the art of making aerogels and can be incorporated herein. Incorporating organosilanes make the resultant aerogels more hydrophobic and less likely to absorb ambient moisture.

The point is to create a fine reticular network of silicon-oxides-silicon-oxides into a cross-linked lattice forming a strong supporting "structural cast" that can be used as a negative cast or mold, a supporting structure, or a positive cast or mold. In this example of the capacitor; final aerogel is incorporated as part of the nonconductive insulation in the final electronic component.

Once the sol-gel is formed, we have created in essence a casting of the TMV rods within the soft gel-sol matrix. At this point the matrix is washed with several changes of an ethanolic mixture of 0.001 M ammonium hydroxide, 0.05 M EDTA pH 8.5 and a mixture of proteolytic digestive enzymes, (Trypsin, Chymotrypsin, RNAse, DNAse) in order to digest and easily remove the TMV coat proteins and TMV-RNA. Leaving an open array of vertically aligned 18 nm diameter openings directly over the nitrocellulose array-plate.

After a few volumes washing with deionized water, the array-plate is placed in a pressure chamber filled with 100% Ethanol or Methanol.

Supercritical Carbon Dioxide liquid is then used to remove the remaining alcohol within the gel-sol matrix and dry the silicone gel converting it into an rigid aerogel as follows:

The system is pressurized to at least 750-850 psi with $CO_2$ and cooled to 5-10 degrees C. Liquid $CO_2$ is then flushed through the vessel until all traces of alcohol has been removed from the gel-sol matrix.

When the gel-sol is alcohol free, the vessel is heated to a temperature above the critical temperature of $CO_2$ (31 degrees C.). As the vessel is heated the pressure of the system rises. $CO_2$ is carefully released to maintain a pressure slightly above the critical pressure of $CO_2$ (1050 psi). The system is held at these conditions for a short time, followed by the slow, controlled release of $CO_2$ to ambient pressure. As with previous steps, the length of time required for this process is dependent on the thickness of the gel-sol. The process may last anywhere from 12 to 72 hours depending upon the total amount of silicon gel being dried.

Special precautions regarding aerogels: Aerogels can collapse by rehydration with water or other solvents. The surface tensions created by water or other solvents can cause the fine reticular structure of the aerogel matrix to collapse like popcorn in water. The great physical features of the architecture may be destroyed by the surface tensions created in the fine reticular aerogel spaces by solvents (water) and collapsing the cavity matrix.

The way to work around this is to always rehydrate or re-solvate the aerogels starting with supercritical carbon dioxide and adding solvents in the exact reverse to the drying process. This will preserve the structural geometry and strength of the aerogel matrix.

In another embodiment the TMV proteins are removed from the array-plate matrix by proteolytic digestion (the array-plate is now made up of a negative cast of 18 nm diameter TMV coat protein rods) any remaining protein components can be removed by oxidative vaporization, destructive distillation, laser vaporization and can be also be used to clean the array-plate. Aerogels are extremely stable to very high temperatures.

In another embodiment the aerogel is cast around the viral protein, or macromolecular peptide structures, and carbon or boron nitride nanotubes are grown directly within the 4 nm center channels of the TMV protein after the dehydrated aerogel is properly formed and after the supercritical drying.

The array-plate (aerogel matrix) is placed in the PECVD chamber and heated. The temperature is gradually raised from room temperature in air until 600 C. in a gradually increasing oxygen atmosphere in order to oxidize and vaporize any of the remaining TMV proteins and RNA nucleic acids along with the nitrocellulose, leaving the Ferric Nitrate molecules now exposed in direct contact with the 20 nm gold (or other metal) wiring array.

Several methods of vapor deposition can be used to grow nanotubes. In this embodiment, plasma enhanced chemical vapor deposition is used above 550 C. The PECVD method allows the carbon nanotubes to grow from the catalyst metal vertically. Since the vertical pore size from the TMV coat protein rod is 18 nm and very large, a smaller concentration such as 20-30 mM solutions of Ferric Nitrate catalyst can be used, less dense arrays of carbon nanotubes are grown. This works best if methane gas is used and the nanotubes are grown at lower temperatures.

Both positive and negative sides of thick gold bar contacts are connected to the negative of a DC power supply so that the bias current can be controlled to initiate carbon nanotube growth.

Changing the carbon nanotube growth conditions results in different nanotube morphology, with a temperature of 650 C. and pressure of 3 Torr, using 20-30 sscm Methane and 80 sccm of Hydrogen gas, with a bias voltage of −550V to −600V (400 W 700 mA) for 12-15 minutes would be suitable conditions to develop the carbon nanotube array.

Depending up the desired properties of the final electronic component being manufactured, large multiwall carbon nanotubes can be made by switching from methane and hydrogen gas to other gases, such as ethane, ethylene, propane, propylene, and ammonia (NH3) instead of hydrogen gas can be used. Increasing the bias voltage and amperage will make for thicker tubes, and increasing temperature will make for more rapid tube formation. Arrays of carbon nanotube fibers can predominate, or if carbon monoxide and hydrogen are used with sparse catalyst seeding, single wall tubes can predominate.

After 12-15 minutes growth, if tubes of uniform length are desired, these can be obtained by reducing the temperature to 50-70 C. and converting the gas stream to 1% Fluorine gas in Helium for 2 hours. This will deposit fluorine into the terminal regions of grown nanotubes. The gas is switched over to Argon instead of the Helium and the temperature is raised quickly to 1,000 C. cutting the tubes and sealing the ends in the process.

Another method is to use a laser from the side to ablate the tube tips rising above the surface of the aerogel. NdYag laser in a 0.5% oxygen in Helium atmosphere will burn the tips to the desired length.

Once the desired carbon nanotube array is grown, it is checked for short circuits, and once shorts are mapped cutting points pre-engineered into the minor wiring branch points can be ablated, as originally designed into the gold (or other metal) circuit design to the open the short. After testing and short circuit ablation, the carbon nanotube array-plate is potted/sealed in a waterproof epoxy coating for use.

Example 2

Figure 12:
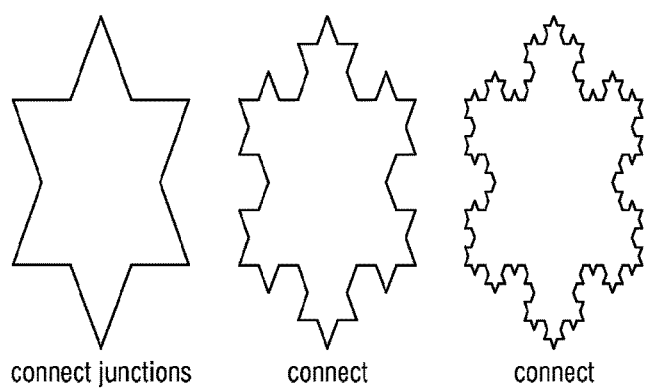
FIG. 12 shows negative or positive lithographic mask material is made with any pattern geometries desired based on the gain, band, and resonant frequency of the desired antenna such as these.

Fractal Antenna Array:

In another embodiment, smaller peptides, such as closed purified preformed GFP barrels or the longer and wider previously described s-barrel proteins are arrayed on their own custom made in situ graphene surface. The way this is done is as follows:

A negative or positive lithographic mask material is made with any pattern geometries desired based on the gain, band, and resonant frequency of the desired antenna such as these: FIG. 12

In this example a wet plasma etching technique using a positive photoresist such as Shipley 1813 or 1827, after exposure and development, will block the aqueous etch solution (KOH 99%+1% Isopropanol). Then cut an anisotropic channel in the fractal pattern as laid out on a silicon wafer material. The depth of the anisotropic channel is 50-900 nm depending on the type of nanotube and the array density required.

Preferably Gold, but Silver, Tin, Aluminum, Nickel, or Copper, (600 nm thickness Copper would be used if the first conductive bonding layer is to be made of graphene) or other alloys may be plated to a thickness of 50-700 nm into the previously etched channel. This is then cleaned using RCA, weak HNA, or organic solvents and clean deionized water, or may also be cleaned by brief oxygen plasma etch in preparation for the next layer.

In the fractal antenna array, it should be noted that this would be a two sided antenna, with a layers from top to bottom thus: starting with carbon nanotube-graphene-copper-silicon dioxide-silicon-silicon dioxide-copper-graphene-carbon nanotube and the separation layer between both halves is conductive silicon wafer material. This wafer middle material may be used a common ground plane between each half if desired.

Each half of the fractal-nanotube-array forms one half of the dipole antenna contact and having identical and completely symmetric geometry which will only differ by the slightly uneven and uncontrollable heights of the nanotubes grown. But this does not alter the performance even if they are off by as much as 20%; since the under layer designed bed of copper and the fractal pattern form the basis for the harmonic transmitting and receiving elements of the antenna. The nanotubes act as individual conductive resonant towers, are designed to make the surface area of the array really huge as contained in such a small space.

Once the 600 nm Copper is deposited an aqueous solution of between 10-70% graphene oxide is spin coated into the channel; a 405 nm laser or UV light energy is applied to the graphene oxide solution forming a single layer of graphene sheeting within the etch pattern base directly and directly attached to and on top of the copper layer.

Copper is being used in this example because it is the best material for forming a conductive flat planar connection to the graphene surface, but certainly other metals can be used, and if impedance is desired at the junction this can be controlled by type of nanotube chosen as well.

This is gently rinsed with pure water to remove any remaining unreacted graphene oxide solution and vacuum dried, and then a neutral or slightly acidic (pH 4-6) carboxycellulose containing between 0.25-5% carboxycellulose mixed with 20-60 mM Ferric Nitrate (but many other cationic metals can be used if other than single wall carbon nanotubes are desired) is spin coated onto the graphene held on top of the copper layer within the etched channel.

Once the carboxycellulose layer is applied EDC/NHS coupling of the barrel protein to the carboxycellulose can be achieved as follows:

2 mM 1-Ethyl-3-[3-dimethylaminopropyl]carbodiimide hydrochloride (EDC or EDAC), which is also known as is a "zero-length" crosslinking agent, in a suitable buffer (0.1M MES (2-[morpholino]ethanesulfonic acid, 0.5M NaCl, pH 4.7-6.0) reacts with the free carboxy groups on the carboxycellulose to form a o-acylisourea, which is then stabilized by +/−5 mM NHS (N-hydroxysuccinimide) or Sulfo-NHS (N-hydroxysulfosuccinimde) which stabilizes the reactive lifespan of the o-acylisourea for bonding to proteins purposes.

Then the previously described GFP or s-barrel proteins, in this case naturally folded GFP containing the fluorophore, can be used; or a quadruple long s-barrel may be used (these are rod shaped and 4 nm diameter by 8-32 nm length). Each GFP can be bonded to the surface by adding it to water at neutral or slightly alkaline pH and the protein barrel will form a stable ester linkage.

Depending on the diameter of the nanotube growth channel desired, different shaped or sized barrel proteins can be used. The GFP or s-barrel length is selected based on the harmonic of the fractal antenna desired.

The s-barrels may be applied in one length or mixed lengths, based upon the desired gain and characteristics of the antenna. Different length barrels can be ink-jet printed or micro-sprayed onto the reactive EDC/NHS surface to correspond to the fractal arms, or stamp printed by making a TEOS mask set, and applying different length barrel proteins as in ordinary lithographic printing.

To make the antenna more efficient, the smaller fractal cross-lengths can have the smaller s-barrels ink jet printed or stamped using micro-lithographic stamps or ink jet printing methods.

Depositing a thin layer of bond Avidin or Streptavidin in 0.1-2% gelatin or 0.1-5% agarose land spin coat over the metal or graphene layer. Designing the protein of the s-barrel or GFP barrel with a N-terminal or C-terminal "Avidity Tag" which is a 14 amino acid residue linker with an exposed lysine residue designed to accept biotin when directed to this site specific lysine using an enzyme, Bir-A, which will bind the biotin in only one place on tag. The s-barrels will be predominantly aligned in one orientation, and if in sufficient molar ratios are used, will be predominantly vertically arrayed and evenly distributed.

If complete vertical alignment of the barrel protein matrix array is desired, an externally applied electric field as in electrophoresis with voltage differences of 20-250 volts can be applied as barrel proteins are applied and when the TMOS sol-gel is being applied.

A soft silicon gel-sol matrix is formed around the s-barrels by spin coating a thin layer of TEOS and ammonia ethanol solution as described above in Example #1.

Once the gel is formed and is firm, but still in the aqueous phase, the GFP and/or s-barrels can be released from the Avidin if the "Soft-Avidin" (weakly binding avidin mutant) is used and the appropriate releasing buffer applied, then the barrel proteins can be washed away after this un-bonding buffer is applied.

Before the aerogel is completely dried, depending on the type of photoresist used, it may be removed leaving those areas of wafer free of aerogel components (in the photoresist and/or etch protected areas).

The TEOS catalysis is completed and the aerogel casting around the GFP or s-barrel array is processed and then dried as described above, in supercritical carbon dioxide.

The gelatin or agarose is oxidized off the graphene slowly, leaving the Ferric Nitrate nodules open in the "aerogel chimney" bottoms. By slowly heating in air or reduced vapor pressure of oxygen and pulsed to 400-500 C., with care to protect and prevent oxidation of the graphene layer. This heating prepares the graphene layer now with Ferric Nitrate catalyst crystals to begin the nanotube growth process.

If graphene is not used as in the examples above, and nanotubes are simply grown on the remaining metal pattern, then the surface can be oxygen plasma etched at high temperatures to clean the surface of any remaining proteins, leaving only silicon oxides, and metal cations ready for vapor deposition processing.

If the antenna array is desired to be connected up with graphene, the nanotubes are then grown on the graphene layer using the "aerogel chimneys" as perpendicular growth guides. Suitable catalysts can be applied, then a surface mask can be applied with photoresists as is usual in multi-layer deposition and etching as is known to those skilled in this type of manufacture.

This desired result is a layer of precisely aligned and equally spaced, aerogel insulated and separated nanotubes growing out of an array of graphene sheet, firmly grounded or in excellent electrical contact with of copper.

Example 3

Longer Tubes:

Using the product of Example #1 or Example #2 above provides a uniform distribution of aligned similarly sized and type of nanotubes in array, the length can be increased indefinitely using the nanotubes themselves as growth guides as follows:

Taking the product of nanotubes grown in Example #1 the nanotubes (280-300 nm in height, can be grown above the plane of the aerogel by longer vapor deposition times, for example gown to 350-400 nm in height. To stabilize this array, another layer of TEOS is spin coated and used to form an aerogel supporting and insulating structure around the protruding nanotube tips, then this can be hardened and again, super-critically dried, and the aerogel tops are themselves used as the growing points for longer nanotubes. This process can be repeated to obtain very stable and long nanotubes, pre-enclosed in the best known capacitor insulator, aerogel material.

Deuterium labeled Nanotubes can be grown using a stream of Deuterium gas (D2), Deuterated Methane (CD4), or Deuteriated Ammonia and/or Deuterium Oxide (D2O) in the gas stream mixtures. Deuterium grown Carbon Nanotubes will have subtly different properties due to the increased density and of the extra neutron.

Tritiated carbon nanotubes or other types of nanotubes can also be made in a similar way, using Tritiated Ammonium (NT4), Tritiated (T2) hydrogen instead of hydrogen gas, or Tritiated Methane (CT4) and these may find some utility in fusion reaction research, biological research, and will have definite electronic benefits since entrapped Tritium emits electrons, since they are not of very high energy, these will be absorbed as they are generated by the array of carbon-nanotubes surrounding them and capturing their spontaneous emission. The resulting device would be a self-generating battery, where the decay of the Tritium will power the battery. These emitted electrons can do work, or provide luminescence standards once tools are made using coated phosphors, or zinc sulphide compounds to coat them.

Example 4

Sorting nanotubes by diameter

S-barrel hydrophobic center arrays can be used as a sieve to sort, hold, and align nanotubes in solution. A circular matrix of s-barrels placed on a support such as Whatman membranes of larger diameters can be designed to allow gravity and/or centrifugal force to separate nanotubes by a combination of forces.

Since the s-barrels can be aligned into a regular arrayed lattice, using functional R-groups designed into their peptide backbone, these can interlock to form a "north-south" covalent or hydrogen bonded junction, "east-west" covalent or hydrogen bonded junction and the amino (N) and carboxy (C) terminals of the peptide chain can be modified with "click chemistries", poly-histadine tags that bind Cobalt or Nickel (that may be used as catalysts to grow nanotubes, remaining in place after their associated peptide's removal, or various types of silano-amino or sulphydryl chemistry (additions of cysteine amino-acid residues). Functionalization of these arrays is well known to those skilled in the art and can be predicted by computer modeling.

Once the array of s-barrels is made, these can be used as filtration sieves, since their diameters can be precisely controlled by the addition of extra s-barrel staves circumferentially, holding the array rigidly in place with a polymer or aerogel, backing them on a support with larger pore diameter, the nanotubes can be centrifuged through vertical plate like layers stacked in a centrifuge tube. The s-barrel proteins will only allow the tubes of specified diameter to pass. The smallest Single Wall Nanotubes can be obtained in high purity by the construction of these barrel protein arrays.

Control of the passage of chiral, arm chair, or "zig-zag" nanotubes can be partially purified by the polar and non-polar groups spatial arrangements inside the tube. Making a spiral arrangement of non-polar r-groups on the inside of the s-barrel will facilitate the passage of for example Chiral nanotubes, most should have hydrophobic interiors and be stable in nonpolar solvents.

The other benefit of using s-barrels proteins as nanotube sieves is the ease at which they can be mutated and the mutations can be screened and selected to hold nanotubes of one spatial geometric orientation, by making millions of DNA mutations encoding the barrel's, and screening in high-throughput manner.

Electronic resonance sorting, or micro NMR sorting, similar to fluorescent sorting can be used to determine which s-barrels contain the desired nanotube configuration, and once known, the s-barrel peptide can produced in large amounts by cloning.

Figure 13:
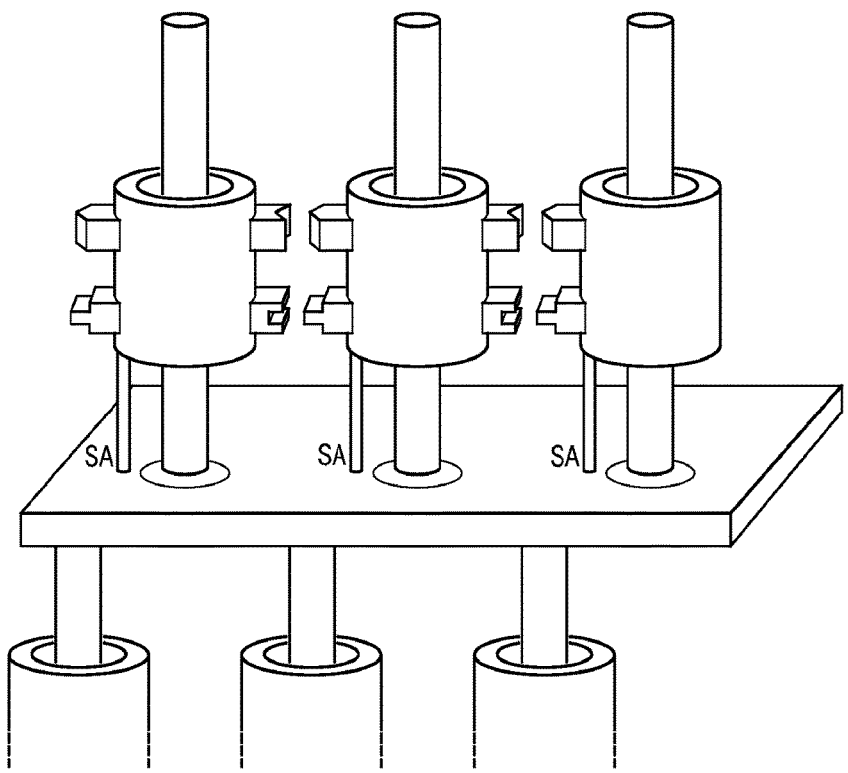
FIG. 13 shows using S-barrels proteins as nanotube sieves.

Example 5 s-barrels-nanotubes as a mechanic-electronic devices:

Another embodiment is the use of s-barrel proteins as holder for single or multi-wall nanotubes. FIG. 13 has a picture of an array of nanotubes, held in spatial array by s-barrels designed with hydrophobic interiors.

Figure 14:
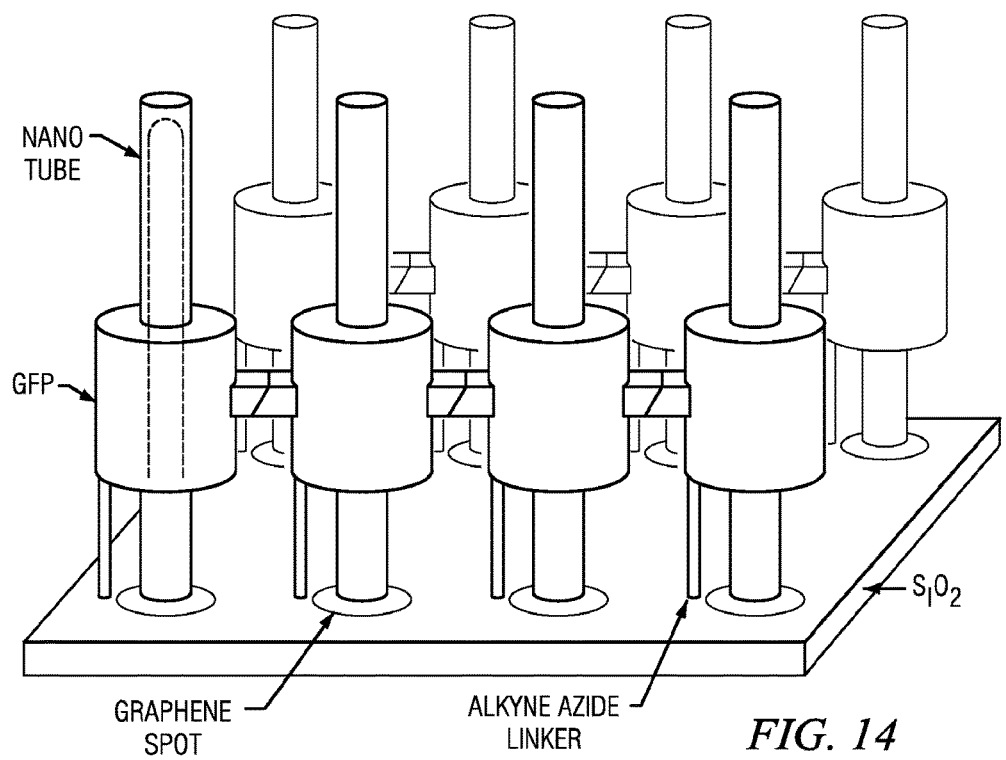
FIG. 14 demonstrates that the nanotubes have been held in an x-y array, with the nanotubes held in vertical orientation, equally spaced, and making a connection to a graphene spot, or grown integrally out of, or in contact with a "graphene spot".

As can be seen in FIG. 14, the nanotubes have been held in an x-y array, with the nanotubes held in vertical orientation, equally spaced, and making a connection to a graphene spot, or grown integrally out of, or in contact with a "graphene spot".

The "graphene-spot" does not have to be graphene, but may be any metal and each spot can be wired from below, as in any silicon wafer etch and prepared by using methods of positive/negative photoresists, and lithography as is well known to those designing and building such circuits and structures.

Another embodiment described is that the nanotubes can also self-assemble into their respective s-barrels by first solubilizing them in a nonpolar solvent, disrupting their aggregation by sonication, and then by slowly adding them in very dilute concentration to the array in a nonpolar solvent such as 100% Ethanol and gradually increasing the polarity of their environment by raising the ionic strength and polarity of the solvent, (adding salt and water) they will try to hide from the polar ionic solvent by self-insertion into the s-barrel array.

Note that the nanotubes free ends are free to vibrate; the s-barrel tube length can be adjusted to dampen the free vibration. The array can be spin-coated with the TEOS in an Ethanol solution and thin layer of nonconductive aerogel can be formed to hold the nanotubes within the s-barrel array in place.

Since each nanotube is in electrical contact with the "under-pavement" electronic circuit, if so desired an alternating radio-frequency (RF) current can be applied to the base of the individual nanotube, and when the frequency spectra is swept the nanotube will start to emit like an individual antenna. This antenna will be resonant with several other nanotubes of equal length and any nanotubes that are in sympathetic (harmonic) resonance with the one stimulated nanotube (once its individual frequency is mapped) all the others in resonance will be mapped and their vibrational frequency will be known and their lengths can be determined.

As each tube has a frequency sweep, the other tubes are mapped and vice versa, once mapped each tube will have a unique signature over the array. This collected set of signatures can be used as a code key, and if nanotubes of variable lengths are used, and inserted at random, each code key will be unique.

Another use for the array depicted in FIG. 13 is each nanotube's RF signature becomes a type of informational digit, and may be used as a unique state, in a way analogous to currently used digital on/off states, for one (1) on and zero (0) off bits, but this array will have many unique digit signatures, so this array can be used as instead of a binary array, but can have N number of digits dependent on the size of the array and variable length of the nanotubes.

Example 6

Luciferase used to generate graphene conductive areas:

The array in FIG. 13 was modeled after the Green Fluorescent Protein (GFP), however in nature the GFP is sometimes associated with a light-emitting enzyme, a luciferase. There are several known Luciferases, all are protein peptide structures, some are similar in size as GFP. Some are smaller (17 KDa) some larger (80 KDa).

One enzyme, Renilla luciferase can oxidize an analog of Coelenterazine to make light and a product chemical called Coelenteramide. If the methoxy-eCoelenterazine analog, or Coelenterazine 400a is used, it makes near UV light of the same frequency that catalyzes the photo-coupling reaction of graphene-oxide to form graphene.

Renilla luciferase also has a binding domain (hydrogen and Van der Waal's) causing it to associate with GFP barrels and in nature exists as a complex. In cases where a small defined spot of graphene is required, 50% graphene oxide in water is used to make large graphene monolayers using a LightScribe laser on plastic surfaces currently. Where very small precise graphene spots are desired, Renilla luciferase can be attached to the array, using standard bioconjugation as described and practiced by a variety of methods by those skilled in the art, and by adding the proper Coelenterazine analog, the luciferases will generate light a few nanometers from the surface and right in the graphene oxide solution, this can be used to grow a graphene spot in a defined loci.

Once the graphene has been deposited, the Luciferase can be unlinked, and the surface prepared by chemical and plasma cleaning methods, or a suitable catalyst. The nanotube can be used to grow nanotubes of one of the three geometries by using only that nanotube mixture on the graphene spots.

Usually graphene is best deposited by plasma chemical vapor deposition on 600 nm thickness copper; however, using luciferase to deposit graphene on a copper connector is also depicted here.

Example 7

Many types of tubular barrel proteins and self-assembling peptide polymers in combination with siloxane or sulphydryl surface (silicon oxide) chemistry can be used to form arrays that can be used directly, to hold the nanotubes, frozen in place with aerogel, and removed either while the aerogel is still in the sol-gel phase, or after the aerogel has been formed and dried and the protein components can be cleaned off by oxygen plasma and Hydrogen gas reduction and oxidation at high temperatures.

These aerogel casts can be placed on wafers and used as masks for guiding the growth of nanotubes.

Example 8

The array of FIG. 13 can be arranged so that s-barrels are in a binary distribution, the result is two nanotubes will be close together, or a tetrad of nanotubes will be bundled, these can form the basis for a field emitter if the appropriate voltage and spectral output phosphor is placed above them on the electron emitting point ends, they can be made into a flat screen display by overlay with a thin plastic film containing a thin coating of phosphors.

Example 9

The arrays of aerogel containing multiwall nanotubes will make excellent cold cathodes for x-ray tubes and other type of cathode tips.

Example 10

Aerogel grown single-wall nanotube array can grow on an array of fine tungsten micro-wires, then broken mechanically and the intact tungsten wire-aerogel holder-nanotube can be visually picked out and used as uniform replaceable atomic-force microscope and atomic forceps tips.

Example 11

Since aerogels are thermally insulating, and nanotubes of particular lengths are very efficient at absorbing infrared light, the same array as depicted in FIG. 13 can be placed on a Sterling cooler, and used in place of a microbolometers (in this case; nanobolometers) with extremely high resolution, and can be used as IR sensors or other types of light based sensors based on the length to frequency ratios of their harmonic resonance.

Example 12

Field emission is hampered by dense collection of nanotubes, since dense closely spaced nanotubes shield the interior remaining nanotubes from the electric field. Using these arrays, larger diameter nanotube arrays, formed as a wall of cylinders around a central nanotube bundle can be used to drive the electric field of the inner bundle. This same array can be used as a capacitor if direct current is applied instead of RF.

Figure 15:
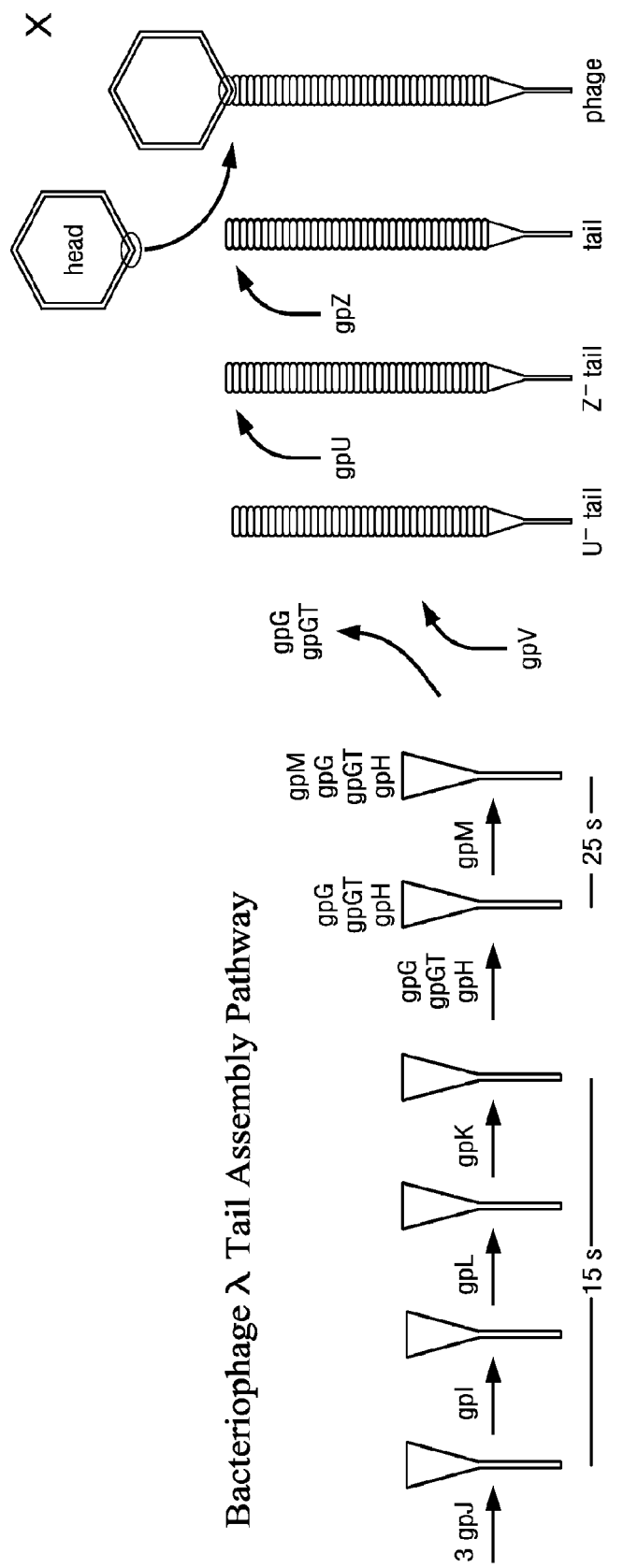
FIG. 15 shows Bacteriophage self-assembly.
Figure 16:
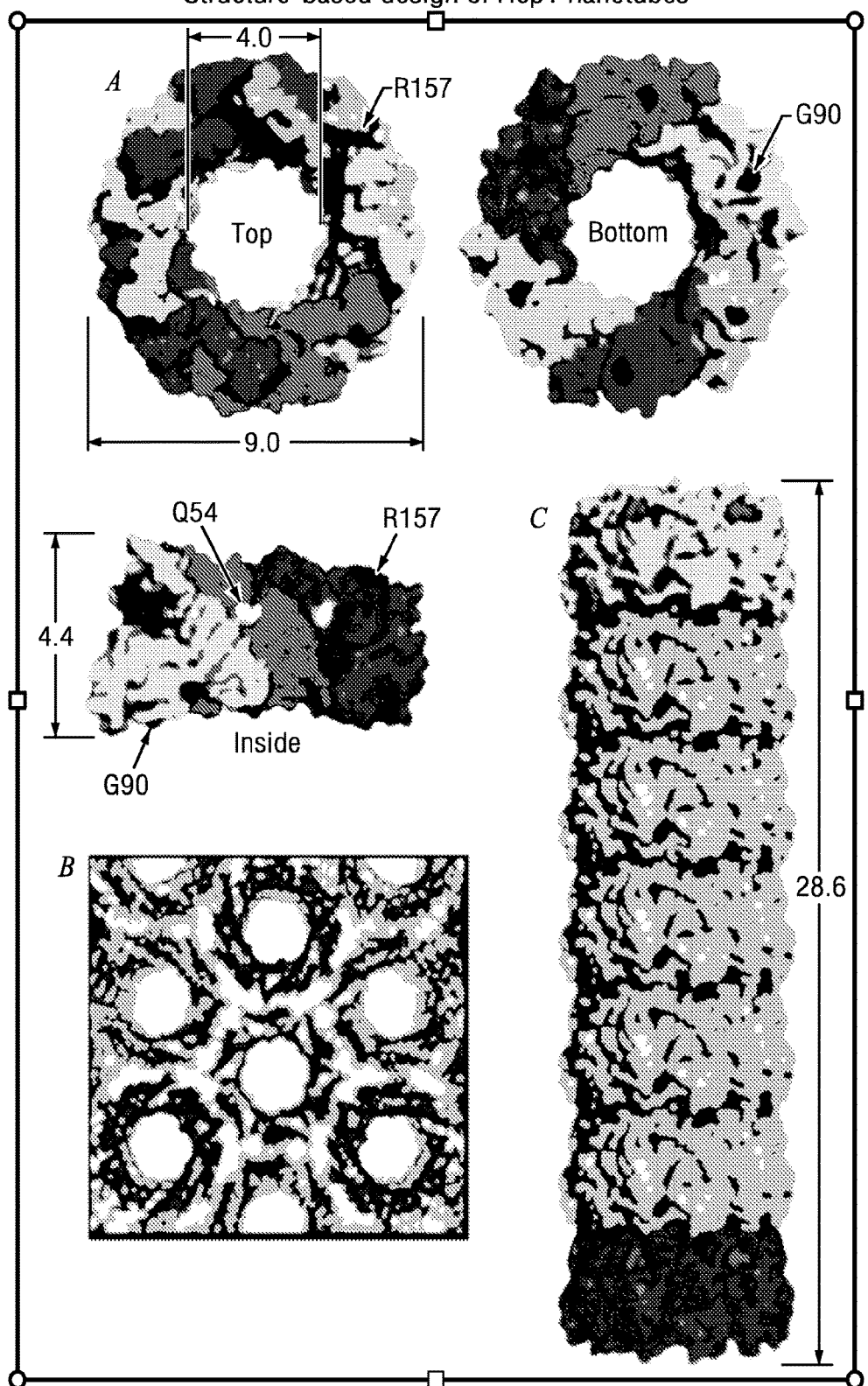
FIG. 16 shows Hcp1 nanotube self-assembly.
Figure 17:
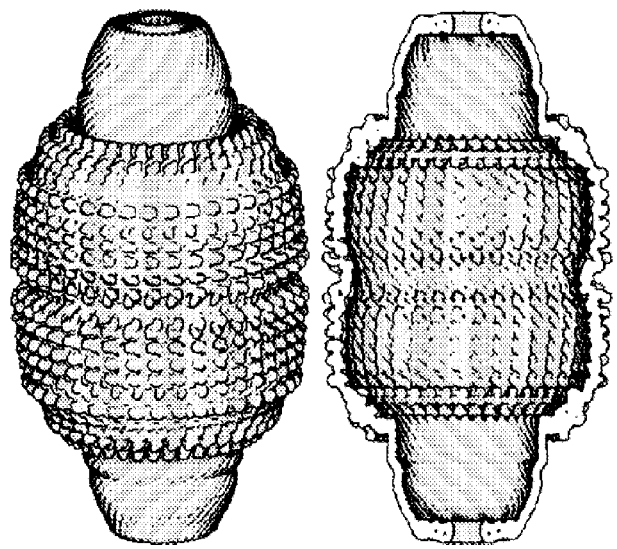
FIG. 17 shows vault proteins.

In General:
Proteins for use comprise, but are not limited to:
FIG. 15 Bacteriophage self-assembly
FIG. 16 Hcp1 nanotube self-assembly
FIG. 17 Vault proteins Example 13

Whispering Gallery micro-cavity Resonators

Using vault proteins, which are self-assembling "cap and barrel proteins" that can reversibly assemble and dissemble based on pH. By disassemble we mean the vault protein opens in the center forming two open basket like proteins.

Figure 18:
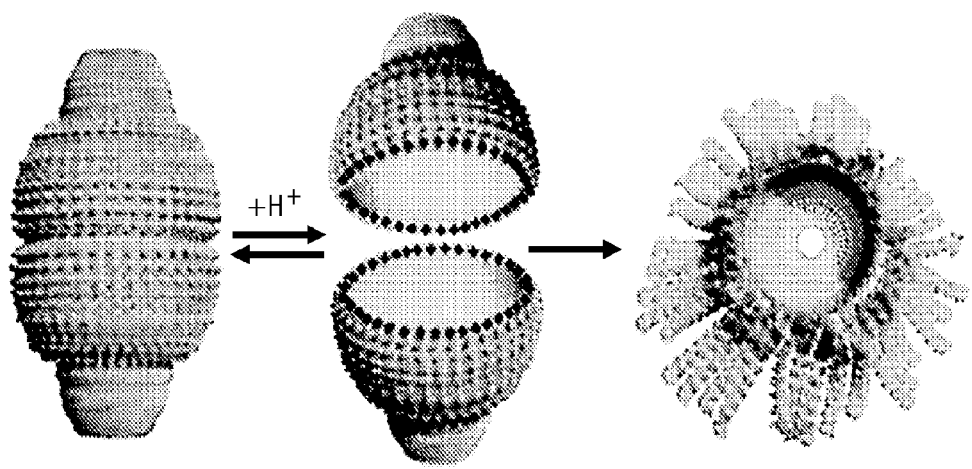
FIG. 18 shows pH dependent opening and reversible closing of vault protein.
Figure 19:
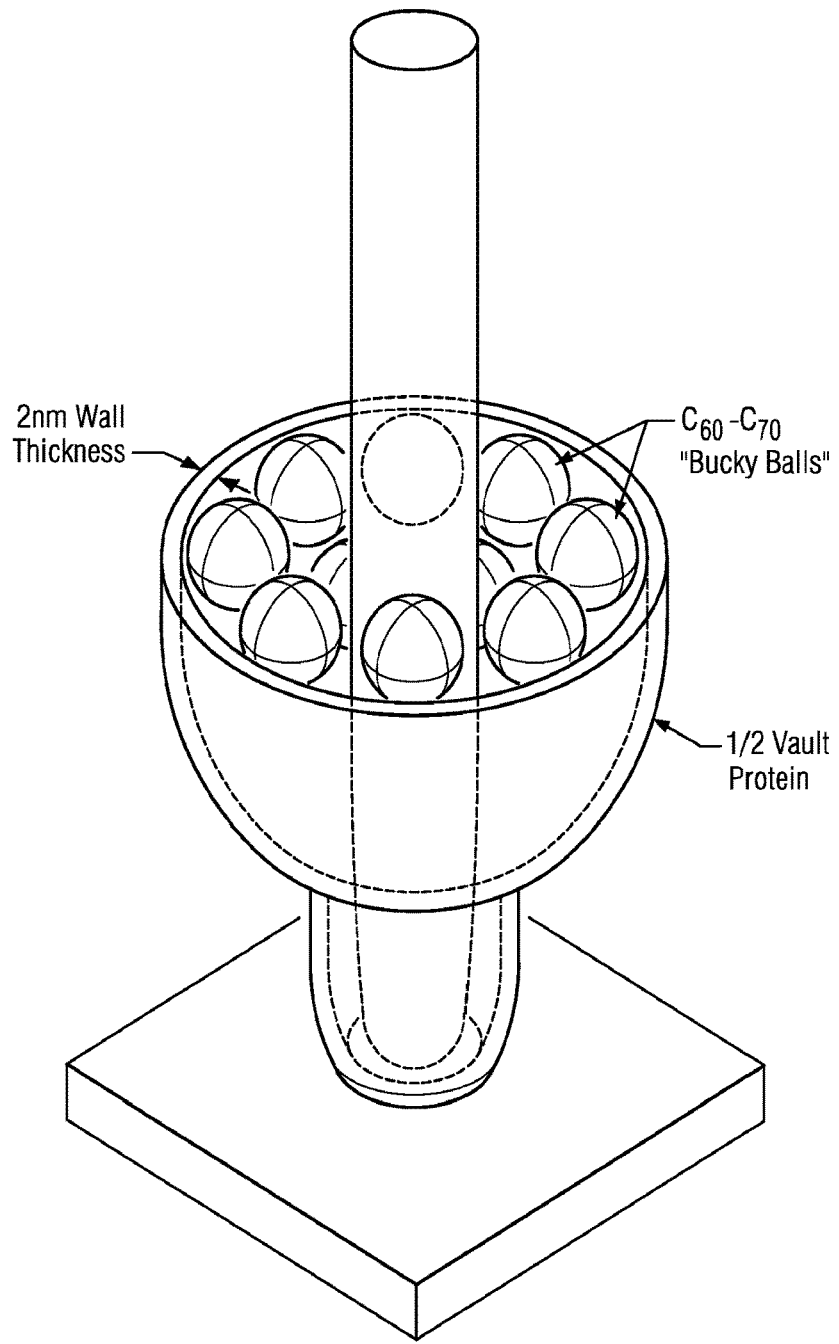
FIG. 19 shows a schematic involving "bucky balls".
Figure 20:
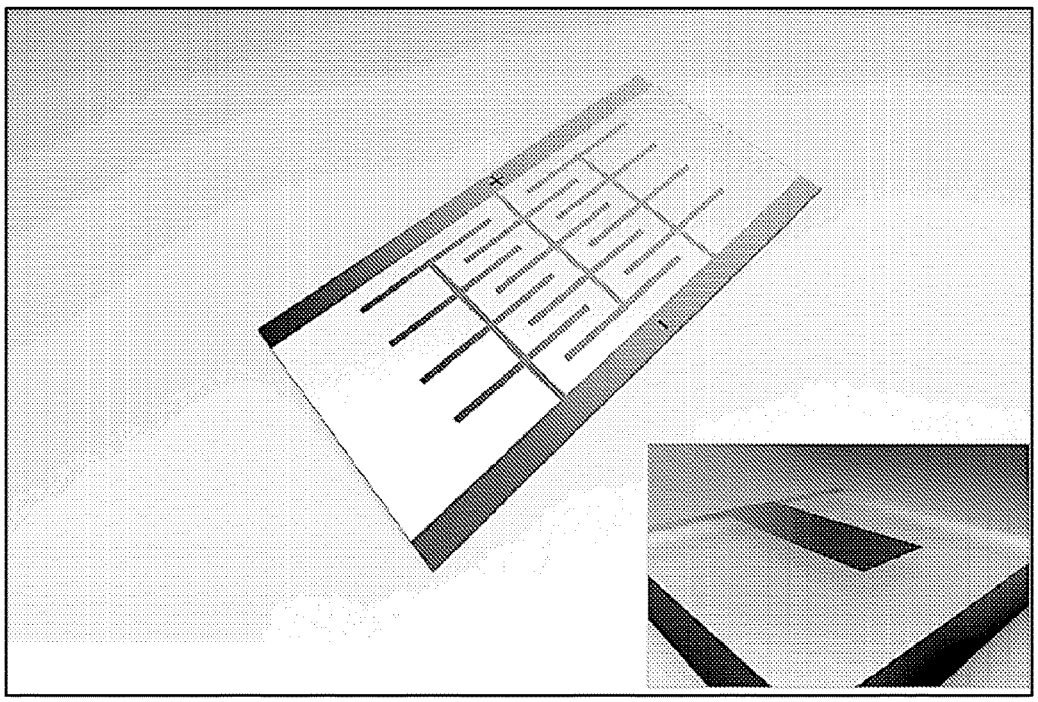
FIG. 20 shows Copper Wiring—Copper wiring laid onto a Silica Dioxide base plate forms the structural element to begin the building of Nano-Tubes.
Figure 21:
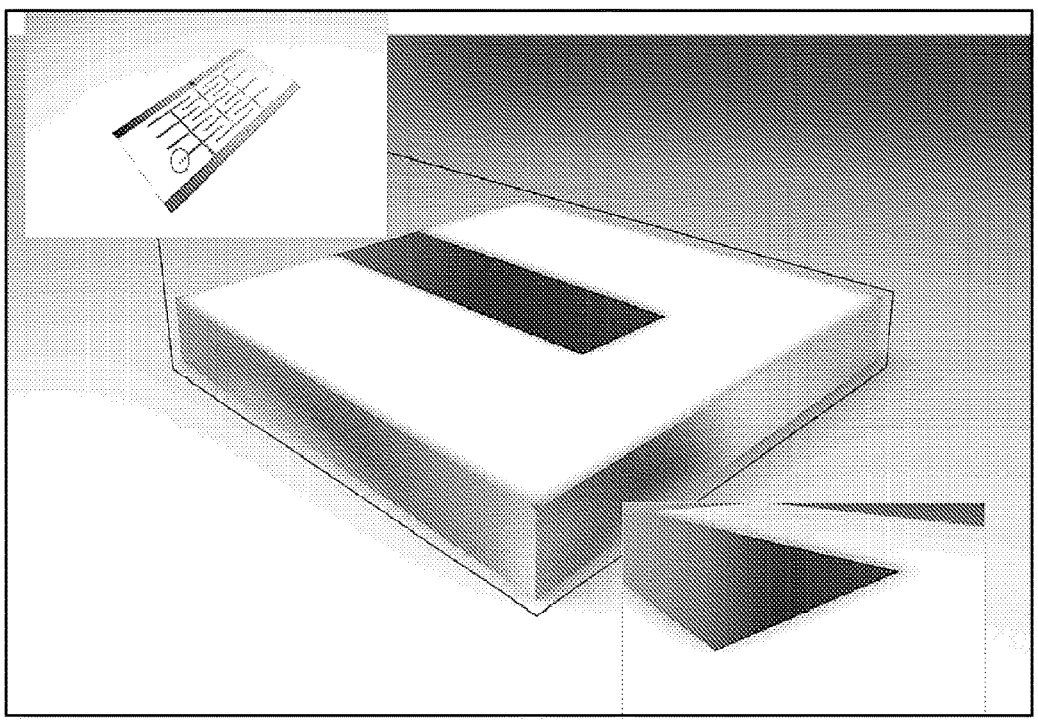
FIG. 21 shows Create Photoresist Mask—Layer the silica base with photoresist mask ready for application of FeNO3. Note: Cut away view showing small section of copper tracking.
Figure 22:
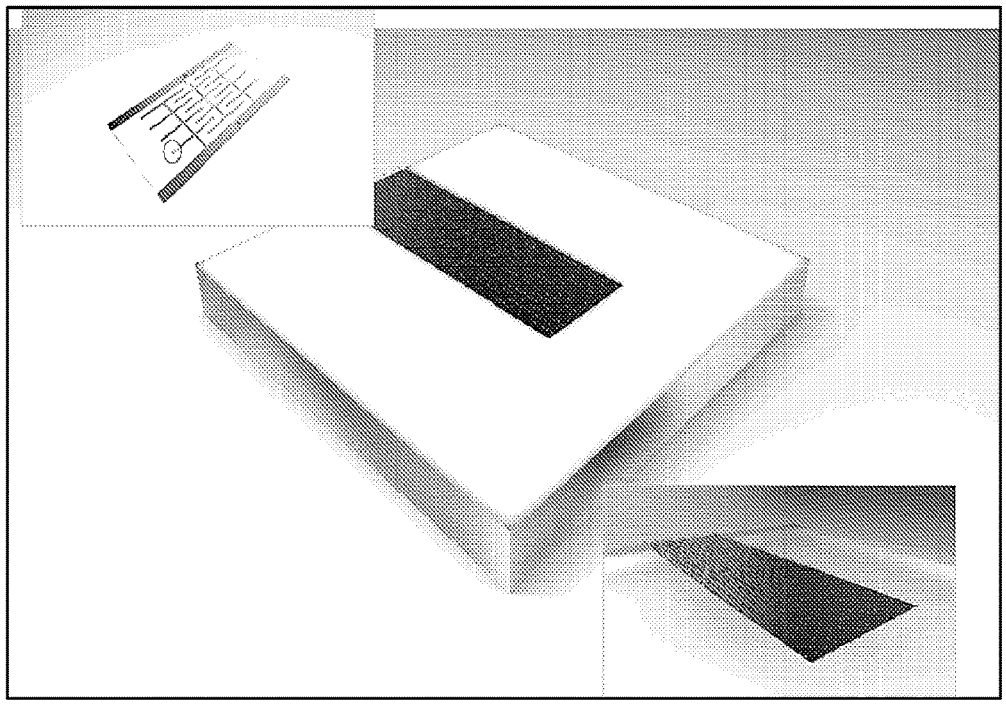
FIG. 22 shows Layer FeNO3—Layer the Cellulose Nitrate with FeNO3.

Into double cap-double barrel protein one to three major vault sub-proteins self-assemble; these vault proteins form by themselves to make basically half of a double barrel shape, then the other half comes in from the open top and the two open tops merge to form the complex double barrel vault. FIG. 18 shows pH dependent opening and reversible closing of vault protein.

Using Baculovirus expressed purified vault protein monomers, it has been shown that this vault protein will self-assemble completely and has even been made as a fusion protein with Firefly Luciferase and Green Lantern Protein.

Vault protein dimensions are 32-42 nm across and 65-75 nm in length. Volume of the vault is $5 \times 10^7$ Angstroms$^3$.

These structures allow an interesting type of new kind of microelectronic component; an electronic version of the well-known in architecture as a capula shaped echo chamber known as "whispering gallery." Spoken sound tends to be captured and goes around and around the copula and the sound energy gradually dissipates slowly over time.

The underlying physics principle has been shown to work in laser fibers touching glass spheres and are known as "micro-cavity resonators." Cavity resonators store energy, and if the electromagnetic field generated by the nanotube pulsed with direct square wave current in one direction can drive the electrons in the Fullerene spheres ("Buckyballs") to spin. This has two effects, one to dampen the incoming harmonic current by impeding it, and two, generating the sp$^2$ orbital electrons to resonate with the magnetic field created by the direct current moving through the nanotube.

By using a nanotube in the center of the capula and surrounding the nanotube by Buckyballs as the electrical current is passed on one direction in the nanotube, a localized magnetic field around the nanotube is created. This field can move the electrons in the Buckyballs, and this energy can be stored as what is named herein as a "whispering gallery micro-cavity resonator array."

As the electrons in the Buckyballs spin they store energy just like any cavity resonator stores energy. This energy will persist after the current in the nanotube is stopped, and can be drawn upon to do work.

The electron's spinning in the Buckyball array should stay in motion as long as no field draws energy off if it, and can be used as memory storage if they can be addressed in isolated groups or as individual vault clusters. There are other uses described below.

To actually build such a whispering-gallery-micro-cavity-resonator-array, Vault proteins can be used as follows:

The N-terminus of the vault protein monomer is made with a poly-histidine sequence made on monomer peptides, each stave of the vault assembly will have an hexa-histidine residue that can be used on a cobalt or nickel ion containing surface to capture the open end at the bottom of the Vault protein. The nickel or cobalt serves a dual purpose; to attach and align the Vault protein so the small end is down forcing the large opening halves facing upward and perpendicular to the nickel or cobalt chloride plane, and the nickel or cobalt is used as the metal catalyst subsequently to grow the nanotubes.

The first step is to make an open vault protein array as described in the preceding paragraph, on a conducting surface or metal surface by vapor deposition, or silicon, and using a gel, agarose, or other solution as described in earlier examples (above). Spin coat the gel on and allow to harden and dry. Wash the surface clean with vault protein solvent buffer, then apply vault protein monomers that do not have the hexa-histidine affinity tags. This will fully form a vault array spaced as close or far as the concentration of the nickel or cobalt concentration applied and the prior vault halves bonded to the gel surface by nickel-histadine hydrogen bonding. Adding the monomer solution in neutral buffer will compete for the open vaults fixed to the silicon support, thus creating an array of vault protein cap-and-barrel structures. Then an aerogel supporting matrix, or just plain silicon matrix using TEOS or MEOS is made and dried. The aerogel is preferred because it will add electrical insulation to the array and is very strong. The problem with the aerogel is the collapse of the matrix by rewetting in water or solvents as mentioned in example 1 (above).

Once the aerogel and vaults are partially solidified, the vault proteins are removed by digestion, and super-critically dried.

Using the catalyst remaining after oxygen plasma cleaning of the entire array, carbon nanotubes can be grown in the center of the vault casting by plasma vapor deposition. The length can be controlled by timing the vapor deposition process so that the nanotubes extend just slightly above the aerogel plane.

A suspension of fullerene "Buckyballs" in heavy water (D$_2$O) and methanol, or hexane, or toluene can be spin coated or soaked onto the opening with the nanotube rising above. Other solvents can be used to affect the deposition concentration of C60 or C70 Buckyballs; however the aerogel will have to be re-solvated using supercritical drying in reverse, gradually increasing the ethanol or toluene concentration so that the aerogel matrix does not collapse.

Dense silicon dioxide can be made with TEOS or other silicon materials can be used in place of aerogel, this will not insulate as well, but forming an aerogel will not be required for all applications.

Solvents such as toluene, hexane, pentane, (many different solvents can be used to control the final concentration of Buckyballs left within the open array).

To obtain higher concentrations of Buckyballs within the empty vault protein cavities, repeated Buckyballs dissolved in solvent is applied and the solvent vacuum dried or gently heated leaving the Buckyballs behind in ever increasing concentration. In this way, solvents such as Toluene, Hexane, and various alcohols that are less toxic can be used.

Once enough of a deposition of Buckyballs are contained within the vault protein cavity spaces, the whole array is dried in vacuum and or heat and vacuum is used to vaporize all the solvents. Care must be taken during this step to avoid drying is aerogel array is required, this would collapse the delicate aerogel matrix, unless as mentioned earlier, reverse crucial drying is used prior to solvating the matrix or a hydrophobic aerogel is used initially.

Buckyballs on the surface of the aerogel can be blown away by pulses of air, tangentially blown across the surface, or washed away by water. Because they are on the outer surface can also be oxidized by mild oxygen plasma exposure and will have to be determined empirically. Mild oxygen plasma can be used to remove the top few Buckyballs on the surface or in the cavity openings.

A conducting layer needs to be applied, as follows; graphene can be vapor deposited by first depositing a layer of aluminum oxide to the matrix and then forming the graphene by vapor deposition. This has the advantage of bonding directly with the nanotubes above the aerogel plane. Other metals such as gold, copper, aluminum can be directly vapor deposited to the aerogel surface.

The aerogel TEOS layer is spin coated to only a few fractions of a nanometer above or below the open surface of the vault protein tops. This will leave a more/less an adjustable 10-20 nm opening for the growth of a nanotube in center of the open empty vault casting, which was the open aerogel cavity after the protein has been digested and oxidized away. The nanotubes are grown to slightly higher than the surface of the aerogel by vapor deposition as previously described to make a better electrical connection to the array.

Once a unidirectional current is applied across the nanotubes, the field will be imparted to the Buckyballs suspended in the vault lying around the nanotubes. These will start to resonate with the electrons spinning around in a similar manner to a whispering gallery photon reflector.

This should add additional stored energy to the array and this energy can be recovered by switching the plates to provide current to do work.

This structure may act like a Tesla Coil in reverse, and energy can be obtained and create a voltage difference across the conducting plates, if the right electromagnetic harmonic field is applied (depending upon the geometric dimensions of the fullerene Buckyballs chosen and length of the nanotube). Electromagnetic energy from the environment can act in a similar manner to the primary coil on a Tesla coil, the fullerene Buckyballs can drive the nanotube to create a higher voltage potential across the plates and this potential can be used to do work.

Another disclosure is to extend the vault proteins, like pearls on a string, by repeating the process of laying down complete vault proteins in aligned arrays one on top of the other, using chemical linkers, such as short complimentary oligomers of DNA for a longer distance between vaults, or the O-acylisourea chemistry, or alkyne-azide linkers for shorter distances, and repeating TEOS gel spin coating to build layer upon layer of vault protein (like beads on a string, only no string). These can be made very long, and a single wall carbon nanotube can be formed in the centers of the array, leaving many Buckyball-containing cavities formed around a single or multiwall nanotube.

With multiwall nanotubes used in these kinds of arrays, the field emission effects are useful, since the wavelength of the resonance frequency harmonic is on the order of 0.6-1.1 nanometers, (essentially the width of a Buckyball), with each Buckyball acting as an independent harmonic antenna.

Example 14

Assembly process of Nano Tubes via TMV RNA mould as shown in FIGS. 20-30:

STEP ONE—Copper Wiring.
STEP TWO—Create Photoresist mask.
STEP THREE—Layer FeNO3.
STEP FOUR—Add TMV RNA.
STEP FIVE—Add Protein Monomers.
STEP SIX—Growth of full TMV Rods.
STEP SEVEN—Add Silica gel-sol.
STEP EIGHT—Digest out TMV Rods.
STEP NINE—Grow Nano-Tubes.
STEP TEN—Panel completion ready for application.
STEP ELEVEN—Stack panels to form battery assembly.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

What is claimed is:

1. A method for making arrays of nanotubes comprising assembling barrel proteins acting as scaffolds and assembling nanotubes wherein the barrel proteins are highly modified barrel proteins to form hydrophobic and hydrophilic channels that guide the nanotubes into the barrel centers, or other geometric patterns utilizing silicone aerogel to form nano-molecular molds, jigs, and surfaces to position nanotubes in precise geometric arrangements and arrays.

* * * * *

SEQUENCE LISTING

```
<160> NUMBER OF SEQ ID NOS: 8

<210> SEQ ID NO 1
<211> LENGTH: 48
<212> TYPE: PRT
<213> ORGANISM: Artificial Sequence
<220> FEATURE:
<223> OTHER INFORMATION: synthetic

<400> SEQUENCE: 1

Phe Lys His Arg Leu Gly Val Ser Ala Ala Thr Ala Val Phe Lys Asn
1               5                   10                  15

Glu Gly Lys Gly Glu Gln Leu Trp Gly Ala Ser Val Leu Ala Ser Thr
            20                  25                  30
```

Arg Lys Ser Phe Asp Tyr Glu Ala Gly Val Val Gln Asp Tyr Glu
            35                  40                  45

<210> SEQ ID NO 2
<211> LENGTH: 38
<212> TYPE: PRT
<213> ORGANISM: Artificial Sequence
<220> FEATURE:
<223> OTHER INFORMATION: synthetic

<400> SEQUENCE: 2

Asn Gly Ile Asp Ala Asn Asp Val Leu Gly Lys Phe Gly His Ala Val
1               5                   10                  15

Ser Val Arg Pro Thr Val Asn Gly Phe Arg Tyr Ala Leu Thr Ala Ala
            20                  25                  30

Val Glu Thr Gln Ser Asn
            35

<210> SEQ ID NO 3
<211> LENGTH: 38
<212> TYPE: PRT
<213> ORGANISM: Artificial Sequence
<220> FEATURE:
<223> OTHER INFORMATION: synthetic

<400> SEQUENCE: 3

His Ser Asn Ser Ala Asp Thr Leu Lys Ala Asp Gln Gln Gln Val Ala
1               5                   10                  15

Val Ser Ala Tyr Leu Ala Asp Asn Asp Tyr Gly Ser Val Leu Arg His
            20                  25                  30

Ile Gln Tyr Lys Glu Ile
            35

<210> SEQ ID NO 4
<211> LENGTH: 37
<212> TYPE: PRT
<213> ORGANISM: Artificial Sequence
<220> FEATURE:
<223> OTHER INFORMATION: synthetic

<400> SEQUENCE: 4

Asn Leu Gly Glu Gln Val Gln His His Arg Lys Tyr Ala Gly Gly Tyr
1               5                   10                  15

Gln Val Phe Phe Gly Gly Asn Lys Tyr Asn Phe Gly Ala His Tyr Ser
            20                  25                  30

Glu Ser Asn His Arg
            35

<210> SEQ ID NO 5
<211> LENGTH: 41
<212> TYPE: PRT
<213> ORGANISM: Artificial Sequence
<220> FEATURE:
<223> OTHER INFORMATION: synthetic

<400> SEQUENCE: 5

Gly Ala Asn Asp Asn Leu Ala Tyr Gln Val Ser Gly Ser Leu Gly Ala
1               5                   10                  15

Phe Glu Pro Ser Asp Tyr Arg Val Ser Ile Leu Arg Ala Glu Pro Glu
            20                  25                  30

Ala Ile Lys Asn Val Gly Leu Tyr Asp
            35                  40

```
<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ser Lys Ser Asp Trp Pro Asn Ile
1               5

<210> SEQ ID NO 7
<211> LENGTH: 86
<212> TYPE: PRT
<213> ORGANISM: Artificial Sequence
<220> FEATURE:
<223> OTHER INFORMATION: synthetic

<400> SEQUENCE: 7

Asp Gly Thr Asp Lys Leu Val Ser Asn Leu Arg Gly Val Arg Leu Lys
1               5                   10                  15

Gly Phe Gly Gly Lys Leu Gly Ile Phe Ser Gln Arg Asn Gly Trp Gly
            20                  25                  30

Ser Asp Thr Gly Ala Ile Ser Ala Lys Gln Glu Val Gln Trp Ile Ala
        35                  40                  45

Lys Leu Gly Asn Gly Leu Asp Glu Gln Gly Lys Phe Gly Ile Lys Ser
    50                  55                  60

Gly Leu Asp Val Ile Gly Thr Ala Thr Thr Val Glu Thr Val Gln Gly
65                  70                  75                  80

Asn Gln His Phe Val Ser
                85

<210> SEQ ID NO 8
<211> LENGTH: 16
<212> TYPE: PRT
<213> ORGANISM: Artificial Sequence
<220> FEATURE:
<223> OTHER INFORMATION: synthetic

<400> SEQUENCE: 8

Arg Ser Thr Glu Val Gly Ala Lys Ile Glu Gly Tyr Leu Ser Val Asp
1               5                   10                  15
```